US006911336B2

(12) United States Patent
Holland et al.

(10) Patent No.: US 6,911,336 B2
(45) Date of Patent: Jun. 28, 2005

(54) GNK INTERACTING AMINO ACID DECARBOXYLASE AND METHODS OF USE THEREOF

(75) Inventors: Pamela M. Holland, Seattle, WA (US); G. Duke Virca, Bellevue, WA (US); Timothy A. Bird, Bainbridge Island, WA (US); Kirsten Garka, Lynnwood, WA (US)

(73) Assignee: Immunex Corporation, Thousand Oaks, CA (US)

( * ) Notice: Subject to any disclaimer, the term of this patent is extended or adjusted under 35 U.S.C. 154(b) by 8 days.

(21) Appl. No.: 09/978,248

(22) Filed: Oct. 16, 2001

(65) Prior Publication Data

US 2002/0197690 A1 Dec. 26, 2002

Related U.S. Application Data

(60) Provisional application No. 60/241,324, filed on Oct. 18, 2000.

(51) Int. Cl.[7] .......................... C12N 9/88; C12N 11/00; G01N 33/573; C07N 16/00; A23D 1/00
(52) U.S. Cl. .......................... 435/232; 435/7.4; 435/174; 435/194; 435/15; 530/387.3; 530/412; 530/388.23; 530/350; 536/23.2
(58) Field of Search .............................. 435/232, 174, 435/7.4; 530/412, 387.3, 388.23, 350; 536/23.2

(56) References Cited

FOREIGN PATENT DOCUMENTS

| WO | WO 97/47750 | 12/1997 |
| WO | WO 00/36097 | 6/2000 |
| WO | WO 01/22920 A | 4/2001 |
| WO | WO 01/53312 A | 7/2001 |
| WO | WO 01/53455 A | 7/2001 |
| WO | WO 00/55174 A | 9/2001 |

OTHER PUBLICATIONS

Vito P. et al. Generation of Anti–apoptotic Presenilin–2 Polypeptides by Alternative Transcription, Proteolysis, and Caspase–3 Cleavage, J. Biol. Chem., 1997, 272, 28315–28320.*

Graves J. D. et al. Caspase–mediated activation and induction of apoptosisby the mammalian Ste20–like kinase Mst1, EMBO J. 1998, 17, 2224–2234.*

Database EMBL–EBI [Online}, European Information Institute, Hinxton, UK; Apr. 25, 1997, Ohara et al., "Human mRNA for KIAA0251, partial cds.;", Database accession No. D87438.

Nagase et al., DNA Research, 3:321–329 (1996).

* cited by examiner

Primary Examiner—Rebecca Prouty
Assistant Examiner—Malgorzata A. Walicka
(74) Attorney, Agent, or Firm—Paul B. Tran; Stuart L. Watt; Ron K. Levy

(57) ABSTRACT

The present invention discloses a novel polypeptide that contains an amino acid decarboxylase domain, and is a substrate for caspase-3. Nucleic acids that encode the novel polypeptide and antibodies to the polypeptide are also part of the present invention. Methods of using the polypeptide, the nucleic acids and antibodies are also provided.

13 Claims, 5 Drawing Sheets

SEQUENCE LISTING

<160> NUMBER OF SEQ ID NOS: 27

<210> SEQ ID NO 1
<211> LENGTH: 2367
<212> TYPE: DNA
<213> ORGANISM: Homo sapien

<400> SEQUENCE: 1

| | | | | | |
|---|---|---|---|---|---|
| atggacgcgt | ccctggagaa | gatagcagac | cccacgttag | ctgaaatggg | aaaaaacttg | 60 |
| aaggaggcag | tgaagatgct | ggaggacagt | cagagaagaa | cagaagagga | aaatggaaag | 120 |
| aagctcatat | ccggagatat | tccaggccca | ctccagggca | gtgggcaaga | tatggtgagc | 180 |
| atcctccagt | tagttcagaa | tctcatgcat | ggagatgaag | atgaggagcc | ccagagcccc | 240 |
| agaatccaaa | atattggaga | acaaggtcat | atggctttgt | tgggacatag | tctgggagct | 300 |
| tatatttcaa | ctctggacaa | agagaagctg | agaaaactta | caactaggat | actttcagat | 360 |
| accaccttat | ggctatgcag | aattttcaga | tatgaaaatg | ggtgtgctta | tttccacgaa | 420 |
| gaggaaagag | aaggacttgc | aaagatatgt | aggcttgcca | ttcattctcg | atatgaagac | 480 |
| ttcgtagtgg | atggcttcaa | tgtgttatat | aacaagaagc | ctgtcatata | tcttagtgct | 540 |
| gctgctagac | ctgcctgggc | caatacctt | tgtaatcagc | tcggcttgcc | cttcccctgc | 600 |
| ttgtgccgtg | taccctgtaa | cactgtgttt | ggatcccagc | atcagatgga | tgttgccttc | 660 |
| ctggagaaac | tgattaaaga | tgatatagag | cgaggaagac | tgcccctgtt | gcttgtcgca | 720 |
| aatgcaggaa | cggcagcagt | aggacacaca | gacaagattg | ggagattgaa | agaactctgt | 780 |
| gagcagtatg | gcatatggct | tcatgtggag | ggtgtgaatc | tggcaacatt | ggctctgggt | 840 |
| tatgtctcct | catcagtgct | ggctgcagcc | aaatgtgata | gcatgacgat | gactcctggc | 900 |
| ccgtggctgg | gtttgccagc | tgttcctgcg | gtgacactgt | ataaacacga | tgaccctgcc | 960 |
| ttgactttag | ttgctggtct | tacatcaaat | aagcccacag | acaaactccg | tgccctgcct | 1020 |
| ctgtggttat | ctttacaata | cttgggactt | gatgggtttg | tggagaggat | caagcatgcc | 1080 |
| tgtcaactga | gtcaacggtt | gcaggaaagt | ttgaagaaag | tgaattacat | caaaatcttg | 1140 |
| gtggaagatg | agctcagctc | cccagtggtg | gtgttcagat | ttttccagga | attaccaggc | 1200 |
| tcagatccgg | tgtttaaagc | cgtcccagtg | cccaacatga | caccttcagg | agtcggccgg | 1260 |
| gagaggcact | cgtgtgacgc | gctgaatcgc | tggctgggag | aacagctgaa | gcagctggtg | 1320 |
| cctgcaagcg | gcctcacagt | catggatctg | aagctgagg | gcacgtgttt | gcggttcagc | 1380 |
| cctttgatga | ccgcagcagt | tttaggaact | cggggagagg | atgtggatca | gctcgtagcc | 1440 |
| tgcatagaaa | gcaaactgcc | agtgctgtgc | tgtacgctcc | agttgcgtga | agagttcaag | 1500 |
| caggaagtgg | aagcaacagc | aggtctccta | tatgttgatg | accctaactg | gtctggaata | 1560 |
| ggggttgtca | ggtatgaaca | tgctaatgat | gataagagca | gtttgaaatc | agatcccgaa | 1620 |
| ggggaaaaca | tccatgctgg | actcctgaag | aagttaaatg | aactggaatc | tgacctaacc | 1680 |
| tttaaaatag | gccctgagta | taagagcatg | aagagctgcc | tttatgtcgg | catggcgagc | 1740 |
| gacaacgtcg | atgctgctga | gctcgtggag | accattgcgg | ccacagcccg | ggagatagag | 1800 |
| gagaactcga | ggcttctgga | aaacatgaca | gaagtggttc | ggaaaggcat | tcaggaagct | 1860 |
| caagtggagc | tgcagaaggc | aagtgaagaa | cggcttctgg | aagaggggt | gttgcggcag | 1920 |
| atccctgtag | tgggctccgt | gctgaattgg | ttttctccgg | tccaggcttt | acagaaggga | 1980 |
| agaacttttta | acttgacagc | aggctctctg | gagtccacag | aacccatata | tgtctacaaa | 2040 |

-continued

```
gcacaaggtg caggagtcac gctgcctcca acgccctcgg gcagtcgcac caagcagagg    2100
cttccaggcc agaagccttt taaaaggtcc ctgcgaggtt cagatgcttt gagtgagacc    2160
agctcagtca gtcacattga agacttagaa aaggtggagc gcctatccag tgggccggag    2220
cagatcaccc tcgaggccag cagcactgag gacacccag gggctcccag ccctcagcac     2280
accgaccaga ccgaggcctt ccagaaaggg gtcccacacc cagaagatga ccactcacag    2340
gtagaaggac cggagagctt aagatga                                         2367
```

<210> SEQ ID NO 2
<211> LENGTH: 788
<212> TYPE: PRT
<213> ORGANISM: Homo sapien

<400> SEQUENCE: 2

```
Met Asp Ala Ser Leu Glu Lys Ile Ala Asp Pro Thr Leu Ala Glu Met
1               5                   10                  15

Gly Lys Asn Leu Lys Glu Ala Val Lys Met Leu Glu Asp Ser Gln Arg
            20                  25                  30

Arg Thr Glu Glu Glu Asn Gly Lys Lys Leu Ile Ser Gly Asp Ile Pro
        35                  40                  45

Gly Pro Leu Gln Gly Ser Gly Gln Asp Met Val Ser Ile Leu Gln Leu
    50                  55                  60

Val Gln Asn Leu Met His Gly Asp Glu Asp Glu Pro Gln Ser Pro
65                  70                  75                  80

Arg Ile Gln Asn Ile Gly Glu Gln Gly His Met Ala Leu Leu Gly His
                85                  90                  95

Ser Leu Gly Ala Tyr Ile Ser Thr Leu Asp Lys Glu Lys Leu Arg Lys
            100                 105                 110

Leu Thr Thr Arg Ile Leu Ser Asp Thr Thr Leu Trp Leu Cys Arg Ile
        115                 120                 125

Phe Arg Tyr Glu Asn Gly Cys Ala Tyr Phe His Glu Glu Arg Glu
    130                 135                 140

Gly Leu Ala Lys Ile Cys Arg Leu Ala Ile His Ser Arg Tyr Glu Asp
145                 150                 155                 160

Phe Val Val Asp Gly Phe Asn Val Leu Tyr Asn Lys Lys Pro Val Ile
                165                 170                 175

Tyr Leu Ser Ala Ala Ala Arg Pro Gly Leu Gly Gln Tyr Leu Cys Asn
            180                 185                 190

Gln Leu Gly Leu Pro Phe Pro Cys Leu Cys Arg Val Pro Cys Asn Thr
        195                 200                 205

Val Phe Gly Ser Gln His Gln Met Asp Val Ala Phe Leu Glu Lys Leu
    210                 215                 220

Ile Lys Asp Asp Ile Glu Arg Gly Arg Leu Pro Leu Leu Val Ala
225                 230                 235                 240

Asn Ala Gly Thr Ala Ala Val Gly His Thr Asp Lys Ile Gly Arg Leu
                245                 250                 255

Lys Glu Leu Cys Glu Gln Tyr Gly Ile Trp Leu His Val Glu Gly Val
            260                 265                 270

Asn Leu Ala Thr Leu Ala Leu Gly Tyr Val Ser Ser Val Leu Ala
        275                 280                 285

Ala Ala Lys Cys Asp Ser Met Thr Met Thr Pro Gly Pro Trp Leu Gly
    290                 295                 300

Leu Pro Ala Val Pro Ala Val Thr Leu Tyr Lys His Asp Asp Pro Ala
```

|       |       |       |       |       |       |       |       |       |       |       |       |       |       |       |       |
|---|---|---|---|---|---|---|---|---|---|---|---|---|---|---|---|

```
                305                 310                 315                 320
            Leu Thr Leu Val Ala Gly Leu Thr Ser Asn Lys Pro Thr Asp Lys Leu
                            325                 330                 335
            Arg Ala Leu Pro Leu Trp Leu Ser Leu Gln Tyr Leu Gly Leu Asp Gly
                            340                 345                 350
            Phe Val Glu Arg Ile Lys His Ala Cys Gln Leu Ser Gln Arg Leu Gln
                            355                 360                 365
            Glu Ser Leu Lys Lys Val Asn Tyr Ile Lys Ile Leu Val Glu Asp Glu
                            370                 375                 380
            Leu Ser Ser Pro Val Val Phe Arg Phe Gln Glu Leu Pro Gly
            385                 390                 395                 400
            Ser Asp Pro Val Phe Lys Ala Val Pro Val Pro Asn Met Thr Pro Ser
                            405                 410                 415
            Gly Val Gly Arg Glu Arg His Ser Cys Asp Ala Leu Asn Arg Trp Leu
                            420                 425                 430
            Gly Glu Gln Leu Lys Gln Leu Val Pro Ala Ser Gly Leu Thr Val Met
                            435                 440                 445
            Asp Leu Glu Ala Glu Gly Thr Cys Leu Arg Phe Ser Pro Leu Met Thr
            450                 455                 460
            Ala Ala Val Leu Gly Thr Arg Gly Glu Asp Val Asp Gln Leu Val Ala
            465                 470                 475                 480
            Cys Ile Glu Ser Lys Leu Pro Val Leu Cys Cys Thr Leu Gln Leu Arg
                            485                 490                 495
            Glu Glu Phe Lys Gln Glu Val Glu Ala Thr Ala Gly Leu Leu Tyr Val
                            500                 505                 510
            Asp Asp Pro Asn Trp Ser Gly Ile Gly Val Val Arg Tyr Glu His Ala
                            515                 520                 525
            Asn Asp Asp Lys Ser Ser Leu Lys Ser Asp Pro Glu Gly Glu Asn Ile
                            530                 535                 540
            His Ala Gly Leu Leu Lys Lys Leu Asn Glu Leu Glu Ser Asp Leu Thr
            545                 550                 555                 560
            Phe Lys Ile Gly Pro Glu Tyr Lys Ser Met Lys Ser Cys Leu Tyr Val
                            565                 570                 575
            Gly Met Ala Ser Asp Asn Val Asp Ala Ala Glu Leu Val Glu Thr Ile
                            580                 585                 590
            Ala Ala Thr Ala Arg Glu Ile Glu Glu Asn Ser Arg Leu Leu Glu Asn
                            595                 600                 605
            Met Thr Glu Val Val Arg Lys Gly Ile Gln Glu Ala Gln Val Glu Leu
                            610                 615                 620
            Gln Lys Ala Ser Glu Glu Arg Leu Leu Glu Glu Gly Val Leu Arg Gln
            625                 630                 635                 640
            Ile Pro Val Val Gly Ser Val Leu Asn Trp Phe Ser Pro Val Gln Ala
                            645                 650                 655
            Leu Gln Lys Gly Arg Thr Phe Asn Leu Thr Ala Gly Ser Leu Glu Ser
                            660                 665                 670
            Thr Glu Pro Ile Tyr Val Tyr Lys Ala Gln Gly Ala Gly Val Thr Leu
                            675                 680                 685
            Pro Pro Thr Pro Ser Gly Ser Arg Thr Lys Gln Arg Leu Pro Gly Gln
                            690                 695                 700
            Lys Pro Phe Lys Arg Ser Leu Arg Gly Ser Asp Ala Leu Ser Glu Thr
            705                 710                 715                 720
            Ser Ser Val Ser His Ile Glu Asp Leu Glu Lys Val Glu Arg Leu Ser
                            725                 730                 735
```

```
Ser Gly Pro Glu Gln Ile Thr Leu Glu Ala Ser Ser Thr Glu Gly His
        740                 745                 750

Pro Gly Ala Pro Ser Pro Gln His Thr Asp Gln Thr Glu Ala Phe Gln
        755                 760                 765

Lys Gly Val Pro His Pro Glu Asp His Ser Gln Val Glu Gly Pro
    770                 775                 780

Glu Ser Leu Arg
785

<210> SEQ ID NO 3
<211> LENGTH: 240
<212> TYPE: PRT
<213> ORGANISM: Periwinkle

<400> SEQUENCE: 3

Gly Lys Leu Val Cys Tyr Gly Ser Asp Gln Thr His Thr Met Phe Pro
1               5                   10                  15

Lys Thr Cys Lys Leu Ala Gly Ile Tyr Pro Asn Asn Ile Arg Leu Ile
            20                  25                  30

Pro Thr Thr Val Glu Thr Asp Phe Gly Ile Ser Pro Gln Val Leu Arg
        35                  40                  45

Lys Met Val Glu Asp Asp Val Ala Ala Gly Tyr Val Pro Leu Phe Leu
    50                  55                  60

Cys Ala Thr Leu Gly Thr Thr Ser Thr Thr Ala Thr Asp Pro Val Asp
65              70                  75                  80

Ser Leu Ser Glu Ile Ala Asn Glu Phe Gly Ile Trp Ile His Val Asp
                85                  90                  95

Ala Ala Tyr Ala Gly Ser Ala Cys Ile Cys Pro Glu Phe Arg His Tyr
            100                 105                 110

Leu Asp Gly Ile Glu Arg Val Asp Ser Leu Ser Leu Ser Pro His Lys
        115                 120                 125

Trp Leu Leu Ala Tyr Leu Asp Cys Thr Cys Leu Trp Val Lys Gln Pro
    130                 135                 140

His Leu Leu Leu Arg Ala Leu Thr Thr Asn Pro Glu Tyr Leu Lys Asn
145             150                 155                 160

Lys Gln Ser Asp Leu Asp Lys Val Val Asp Phe Lys Asn Trp Gln Ile
                165                 170                 175

Ala Thr Gly Arg Lys Phe Arg Ser Leu Lys Leu Trp Leu Ile Leu Arg
            180                 185                 190

Ser Tyr Gly Val Val Asn Leu Gln Ser His Ile Arg Ser Asp Val Ala
        195                 200                 205

Met Gly Lys Met Phe Glu Glu Trp Val Arg Ser Asp Ser Arg Phe Glu
    210                 215                 220

Ile Val Val Pro Arg Asn Phe Ser Leu Val Cys Phe Arg Leu Lys Pro
225             230                 235                 240

<210> SEQ ID NO 4
<211> LENGTH: 240
<212> TYPE: PRT
<213> ORGANISM: Camptotheca acuminata

<400> SEQUENCE: 4

His Lys Leu Val Val Tyr Gly Ser Asp Gln Thr His Ser Thr Tyr Ala
1               5                   10                  15

Lys Ala Cys Asn Leu Ala Gly Ile Leu Pro Cys Asn Ile Arg Ser Ile
            20                  25                  30
```

```
Arg Thr Glu Ala Val Ala Asn Phe Ser Leu Ser Pro Asp Ser Leu His
            35                  40                  45

Arg Glu Ile Glu Ala Asp Val Ala Ala Gly Met Val Pro Leu Tyr Leu
 50                  55                  60

Cys Ala Thr Val Gly Thr Thr Ser Thr Thr Ala Ile Asp Ser Leu Ser
 65                  70                  75                  80

Pro Leu Ala Asp Val Ala Asn Asp Tyr Gly Leu Trp Phe His Val Asp
                     85                  90                  95

Ala Ala Tyr Ala Gly Ser Ala Cys Ile Cys Pro Glu Phe Arg His Tyr
                100                 105                 110

Leu Asp Gly Ile Glu Arg Ala Asp Ser Leu Ser Leu Ser Pro His Lys
            115                 120                 125

Trp Leu Ser Tyr Leu Asp Cys Cys Cys Leu Trp Val Lys Arg Pro
        130                 135                 140

Ser Val Leu Val Lys Ala Leu Ser Thr Asp Pro Glu Tyr Leu Lys Asn
145                 150                 155                 160

Lys Pro Ser Glu Ser Asn Ser Val Val Asp Phe Lys Asp Trp Gln Val
                165                 170                 175

Gly Thr Gly Arg Arg Phe Lys Ala Leu Arg Leu Trp Phe Val Met Arg
                180                 185                 190

Ser Tyr Gly Val Ala Asn Leu Gln Ser His Ile Arg Ser Asp Ile Gln
            195                 200                 205

Met Ala Lys Met Phe Glu Glu Phe Val Asn Ser Asp Pro Arg Phe Glu
210                 215                 220

Ile Val Pro Arg Val Phe Ser Leu Val Cys Phe Arg Leu Asn Pro
225                 230                 235                 240

<210> SEQ ID NO 5
<211> LENGTH: 240
<212> TYPE: PRT
<213> ORGANISM: Arabidopsis thaliana

<400> SEQUENCE: 5

Glu Lys Leu Val Val Tyr Ser Ser Asp Gln Thr His Ser Ala Leu Gln
 1               5                  10                  15

Lys Ala Cys Gln Ile Ala Gly Ile His Pro Glu Asn Cys Arg Val Leu
            20                  25                  30

Thr Thr Asp Ser Ser Thr Asn Tyr Ala Leu Arg Pro Glu Ser Leu Gln
            35                  40                  45

Glu Ala Val Ser Arg Asp Leu Glu Ala Gly Leu Ile Pro Phe Phe Leu
 50                  55                  60

Cys Ala Asn Val Gly Thr Thr Ser Ser Thr Ala Val Asp Pro Leu Ala
 65                  70                  75                  80

Ala Leu Gly Lys Ile Ala Asn Ser Asn Gly Ile Trp Phe His Val Asp
                 85                  90                  95

Ala Ala Tyr Ala Gly Ser Ala Cys Ile Cys Pro Glu Tyr Arg Gln Tyr
                100                 105                 110

Ile Asp Gly Val Glu Thr Ala Asp Ser Phe Asn Met Asn Ala His Lys
            115                 120                 125

Trp Phe Leu Thr Asn Phe Asp Cys Ser Leu Leu Trp Val Lys Asp Gln
        130                 135                 140

Asp Ser Leu Thr Leu Ala Leu Ser Thr Asn Pro Glu Phe Leu Lys Asn
145                 150                 155                 160

Lys Ala Ser Gln Ala Asn Leu Val Val Asp Tyr Lys Asp Trp Gln Ile
```

-continued

```
                165                 170                 175
Pro Leu Gly Arg Arg Phe Arg Ser Leu Lys Leu Trp Met Val Leu Arg
            180                 185                 190

Leu Tyr Gly Ser Glu Thr Leu Lys Ser Tyr Ile Arg Asn His Ile Lys
        195                 200                 205

Leu Ala Lys Glu Phe Glu Gln Leu Val Ser Gln Asp Pro Asn Phe Glu
    210                 215                 220

Ile Val Thr Pro Arg Ile Phe Ala Leu Val Cys Phe Arg Leu Val Pro
225                 230                 235                 240

<210> SEQ ID NO 6
<211> LENGTH: 232
<212> TYPE: PRT
<213> ORGANISM: Homo sapien

<400> SEQUENCE: 6

Ala Arg Leu Val Ala Tyr Ala Ser Asp Gln Ala His Ser Ser Val Glu
1               5                   10                  15

Lys Ala Gly Leu Ile Ser Leu Val Lys Met Lys Phe Leu Pro Val Asp
            20                  25                  30

Asp Asn Phe Ser Leu Arg Gly Glu Ala Leu Gln Lys Ala Ile Glu Glu
        35                  40                  45

Asp Lys Gln Arg Gly Leu Val Pro Val Phe Val Cys Ala Thr Leu Gly
    50                  55                  60

Thr Thr Gly Val Cys Ala Phe Asp Cys Leu Ser Glu Leu Gly Pro Ile
65                  70                  75                  80

Cys Ala Arg Glu Gly Leu Trp Leu His Ile Asp Ala Ala Tyr Ala Gly
                85                  90                  95

Thr Ala Phe Leu Cys Pro Glu Phe Arg Gly Phe Leu Lys Gly Ile Glu
            100                 105                 110

Tyr Ala Asp Ser Phe Thr Phe Asn Pro Ser Lys Trp Met Met Val His
        115                 120                 125

Phe Asp Cys Thr Gly Phe Trp Val Lys Asp Lys Tyr Lys Leu Gln Gln
    130                 135                 140

Thr Phe Ser Val Asn Pro Ile Tyr Leu Arg His Ala Asn Ser Gly Val
145                 150                 155                 160

Ala Thr Asp Phe Met His Trp Gln Ile Pro Leu Ser Arg Arg Phe Arg
                165                 170                 175

Ser Val Lys Leu Trp Phe Val Ile Arg Ser Phe Gly Val Lys Asn Leu
            180                 185                 190

Gln Ala His Val Arg His Gly Thr Glu Met Ala Lys Tyr Phe Glu Ser
        195                 200                 205

Leu Val Arg Asn Asp Pro Ser Phe Glu Ile Pro Ala Lys Arg His Leu
    210                 215                 220

Gly Leu Val Val Phe Arg Leu Lys
225                 230

<210> SEQ ID NO 7
<211> LENGTH: 232
<212> TYPE: PRT
<213> ORGANISM: Rattus rattus

<400> SEQUENCE: 7

Ala Arg Leu Val Ala Tyr Ala Ser Asp Gln Ala His Ser Ser Val Glu
1               5                   10                  15

Lys Ala Gly Leu Ile Ser Leu Val Lys Ile Lys Phe Leu Pro Val Asp
```

-continued

```
                    20                  25                  30
Asp Asn Phe Ser Leu Arg Gly Glu Ala Leu Gln Lys Ala Ile Glu Glu
                35                  40                  45

Asp Lys Gln Gln Gly Leu Val Pro Val Phe Val Cys Ala Thr Leu Gly
    50                  55                  60

Thr Thr Gly Val Cys Ala Phe Asp Lys Leu Ser Glu Leu Gly Pro Ile
65                  70                  75                  80

Cys Ala Arg Glu Gly Leu Trp Leu His Val Asp Ala Ala Tyr Ala Gly
                85                  90                  95

Thr Ala Phe Leu Arg Pro Glu Leu Arg Gly Phe Leu Lys Gly Ile Glu
                100                 105                 110

Tyr Ala Asp Ser Phe Thr Phe Asn Pro Ser Lys Trp Met Met Val His
                115                 120                 125

Phe Asp Cys Thr Gly Phe Trp Val Lys Asp Lys Tyr Lys Leu Gln Gln
                130                 135                 140

Thr Phe Ser Val Asn Pro Ile Tyr Leu Arg His Ala Asn Ser Gly Val
145                 150                 155                 160

Ala Thr Asp Phe Met His Trp Gln Ile Pro Leu Ser Arg Arg Phe Arg
                165                 170                 175

Ser Ile Lys Leu Trp Phe Val Ile Arg Ser Phe Gly Val Lys Asn Leu
                180                 185                 190

Gln Ala His Val Arg His Gly Thr Asp Met Ala Lys Tyr Phe Glu Ser
                195                 200                 205

Leu Val Arg Ser Asp Pro Val Phe Glu Ile Pro Ala Glu Arg His Leu
                210                 215                 220

Gly Leu Val Val Phe Arg Leu Lys
225                 230

<210> SEQ ID NO 8
<211> LENGTH: 235
<212> TYPE: PRT
<213> ORGANISM: Rattus rattus

<400> SEQUENCE: 8

Glu Lys Leu Val Ala Tyr Thr Ser Asp Gln Ala His Ser Ser Val Glu
1               5                   10                  15

Arg Ala Gly Leu Ile Gly Gly Val Lys Ile Lys Ala Ile Pro Ser Asp
                20                  25                  30

Gly Asn Tyr Ser Met Arg Ala Ala Ala Leu Arg Glu Ala Leu Glu Arg
                35                  40                  45

Asp Lys Ala Ala Gly Leu Ile Pro Phe Phe Val Val Thr Leu Gly
    50                  55                  60

Thr Thr Ser Cys Cys Ser Phe Asp Asn Leu Leu Glu Val Gly Pro Ile
65                  70                  75                  80

Cys Asn Gln Glu Gly Val Trp Leu His Ile Asp Ala Ala Tyr Ala Gly
                85                  90                  95

Ser Ala Phe Ile Cys Pro Glu Phe Arg Tyr Leu Leu Asn Gly Val Glu
                100                 105                 110

Phe Ala Asp Ser Phe Asn Phe Asn Pro His Lys Trp Leu Leu Val Asn
                115                 120                 125

Phe Asp Cys Ser Ala Met Trp Val Lys Lys Arg Thr Asp Leu Thr Glu
                130                 135                 140

Ala Phe Asn Met Asp Pro Val Tyr Leu Arg His Ser His Gln Asp Ser
145                 150                 155                 160
```

```
Gly Leu Ile Thr Asp Tyr Arg His Trp Gln Ile Pro Leu Gly Arg Arg
                165                 170                 175

Phe Arg Ser Leu Lys Met Trp Phe Val Phe Arg Met Tyr Gly Val Lys
                180                 185                 190

Gly Leu Gln Ala Tyr Ile Arg Lys His Val Lys Leu Ser His Glu Phe
                195                 200                 205

Glu Ser Leu Val Arg Gln Asp Pro Arg Phe Glu Ile Cys Thr Glu Val
210                 215                 220

Ile Leu Gly Leu Val Cys Phe Phe Arg Leu Lys
225                 230                 235

<210> SEQ ID NO 9
<211> LENGTH: 243
<212> TYPE: PRT
<213> ORGANISM: Rattus rattus

<400> SEQUENCE: 9

Ala Ala Val Pro Arg Leu Ile Ala Phe Thr Ser Glu His Ser His Phe
1               5                   10                  15

Ser Leu Lys Lys Gly Ala Ala Leu Gly Ile Gly Thr Asp Ser Val
                20                  25                  30

Ile Leu Ile Lys Cys Asp Glu Arg Gly Lys Met Ile Pro Ser Asp Leu
                35                  40                  45

Glu Arg Arg Ile Leu Glu Ala Lys Gln Lys Gly Phe Val Pro Phe Leu
            50                  55                  60

Val Ser Ala Thr Ala Gly Thr Thr Val Tyr Gly Ala Phe Asp Pro Leu
65                  70                  75                  80

Leu Ala Val Ala Asp Ile Cys Lys Lys Tyr Lys Ile Trp Met His Val
                85                  90                  95

Asp Ala Ala Trp Gly Gly Gly Leu Leu Met Ser Arg Lys His Lys Trp
                100                 105                 110

Lys Leu Ser Gly Val Glu Arg Ala Asn Ser Val Thr Trp Asn Pro His
                115                 120                 125

Lys Met Met Gly Val Pro Leu Gln Cys Ser Ala Leu Leu Val Arg Glu
            130                 135                 140

Glu Gly Leu Met Gln Ser Cys Asn Gln Met His Ala Ser Tyr Leu Phe
145                 150                 155                 160

Gln Gln Asp Lys His Tyr Asp Leu Ser Tyr Asp Thr Gly Asp Lys Ala
                165                 170                 175

Leu Gln Cys Gly Arg His Val Asp Val Phe Lys Leu Trp Leu Met Trp
                180                 185                 190

Arg Ala Lys Gly Thr Thr Gly Phe Glu Ala His Ile Asp Lys Cys Leu
                195                 200                 205

Glu Leu Ala Glu Tyr Leu Tyr Asn Ile Ile Lys Asn Arg Glu Gly Tyr
210                 215                 220

Glu Met Val Phe Asp Gly Lys Pro Gln His Thr Asn Val Cys Phe Trp
225                 230                 235                 240

Tyr Val Pro

<210> SEQ ID NO 10
<211> LENGTH: 242
<212> TYPE: PRT
<213> ORGANISM: Drosophila melanogaster

<400> SEQUENCE: 10

Phe Asn Ala Lys Pro Leu Ile Ile Phe Thr Ser Glu Asp Ala His Tyr
```

```
                  1               5                  10                 15
              Ser Val Glu Lys Leu Ala Met Phe Met Gly Phe Gly Ser Asp His Val
                          20                  25                 30

Arg Lys Ile Ala Thr Asn Glu Val Gly Lys Met Arg Leu Ser Asp Leu
                          35                  40                 45

Glu Lys Gln Val Lys Leu Cys Leu Glu Asn Gly Trp Gln Pro Leu Met
                          50                  55                 60

Val Ser Ala Thr Ala Gly Thr Thr Val Leu Gly Ala Phe Asp Asp Leu
              65                  70                  75                 80

Ala Gly Ile Ser Glu Val Cys Lys Lys Tyr Asn Met Trp Met His Val
                          85                  90                 95

Asp Ala Ala Trp Gly Gly Ala Leu Met Ser Lys Lys Tyr Arg His
                          100                 105                110

Leu Leu Asn Gly Ile Glu Arg Ala Asp Ser Val Thr Trp Asn Pro His
                          115                 120                125

Lys Leu Leu Ala Ala Ser Gln Gln Cys Ser Thr Phe Leu Thr Arg His
                          130                 135                140

Gln Gln Val Leu Ala Gln Cys His Ser Thr Asn Ala Thr Tyr Leu Phe
              145                 150                 155                160

Gln Lys Asp Lys Phe Tyr Asp Thr Ser Phe Asp Thr Gly Asp Lys His
                          165                 170                175

Ile Gln Cys Gly Arg Arg Ala Asp Val Phe Lys Phe Trp Met Trp
                          180                 185                190

Lys Ala Lys Gly Thr Gln Gly Leu Glu Ala His Val Glu Lys Val Phe
                          195                 200                205

Arg Met Ala Glu Phe Phe Thr Ala Lys Val Arg Glu Arg Pro Gly Phe
              210                 215                 220

Glu Leu Val Leu Glu Ser Pro Glu Cys Thr Asn Ile Ser Phe Trp Tyr
              225                 230                 235                240

Val Pro

<210> SEQ ID NO 11
<211> LENGTH: 241
<212> TYPE: PRT
<213> ORGANISM: Acinetobacter baumannii

<400> SEQUENCE: 11

Ala Glu Ala Met Lys Asn Val Lys Val Ile Cys Ser Glu Asn Ala His
              1               5                   10                 15

Phe Ser Val Gln Lys Asn Met Ala Met Met Gly Met Gly Phe Gln Ser
                          20                  25                 30

Val Val Thr Val Pro Val Asn Glu Asn Ala Gln Met Asp Val Asp Ala
                          35                  40                 45

Leu Glu Lys Thr Met Ala His Leu Gln Ala Glu Gly Lys Val Val Ala
                          50                  55                 60

Cys Val Val Ala Thr Ala Gly Thr Thr Asp Ala Gly Ala Ile His Pro
              65                  70                  75                 80

Leu Lys Lys Ile Arg Glu Ile Thr Asn Lys Tyr Gly Ser Trp Met His
                          85                  90                 95

Ile Asp Ala Ala Trp Gly Gly Ala Leu Ile Leu Ser Asn Thr Tyr Arg
                          100                 105                110

Ala Met Leu Asp Gly Ile Glu Leu Ser Asp Ser Ile Thr Leu Asp Phe
                          115                 120                125

His Lys His Tyr Phe Gln Ser Ile Ser Cys Gly Ala Phe Leu Leu Lys
```

```
            130                 135                 140
Asp Glu Ala Asn Tyr Arg Phe Met His Tyr Glu Ala Glu Tyr Leu Asn
145                 150                 155                 160

Ser Ala Tyr Asp Glu Glu His Gly Val Pro Asn Leu Val Ser Lys Ser
                165                 170                 175

Leu Gln Thr Thr Arg Arg Phe Asp Ala Leu Lys Leu Trp Met Thr Ile
            180                 185                 190

Glu Ser Leu Gly Glu Leu Tyr Gly Ser Met Ile Asp His Gly Val
                195                 200                 205

Lys Leu Thr Arg Glu Val Ala Asp Tyr Ile Lys Ala Thr Glu Gly Leu
            210                 215                 220

Glu Leu Leu Val Glu Pro Gln Phe Ala Ser Val Leu Phe Arg Val Val
225                 230                 235                 240

Pro

<210> SEQ ID NO 12
<211> LENGTH: 181
<212> TYPE: PRT
<213> ORGANISM: homology sequence

<400> SEQUENCE: 12

Met Asp Val Ala Phe Leu Glu Lys Leu Ile Lys Asp Asp Ile Glu Arg
1               5                   10                  15

Gly Arg Leu Pro Leu Leu Val Ala Asn Ala Gly Thr Ala Ala Val
            20                  25                  30

Gly His Thr Asp Lys Ile Gly Arg Leu Lys Glu Leu Cys Glu Gln Tyr
        35                  40                  45

Gly Ile Trp Leu His Val Glu Gly Val Asn Leu Ala Thr Leu Ala Leu
    50                  55                  60

Gly Tyr Val Ser Ser Val Leu Ala Ala Lys Cys Asp Ser Met
65                  70                  75                  80

Thr Met Thr Pro Gly Pro Trp Leu Gly Leu Pro Ala Val Pro Ala Val
                85                  90                  95

Thr Leu Tyr Lys His Asp Asp Pro Ala Leu Thr Leu Val Ala Gly Leu
            100                 105                 110

Thr Ser Asn Lys Pro Thr Asp Lys Leu Arg Ala Leu Pro Leu Trp Leu
        115                 120                 125

Ser Leu Gln Tyr Leu Gly Leu Asp Gly Phe Val Glu Arg Ile Lys His
    130                 135                 140

Ala Cys Gln Leu Ser Gln Arg Leu Gln Glu Ser Leu Lys Lys Val Asn
145                 150                 155                 160

Tyr Ile Lys Ile Leu Val Glu Asp Glu Leu Ser Ser Pro Val Val Val
                165                 170                 175

Phe Arg Phe Phe Gln
            180

<210> SEQ ID NO 13
<211> LENGTH: 19
<212> TYPE: DNA
<213> ORGANISM: Artificial Sequence
<220> FEATURE:
<223> OTHER INFORMATION: primer

<400> SEQUENCE: 13
ggcagatccc tgtagtggg                                          19
```

<210> SEQ ID NO 14
<211> LENGTH: 22
<212> TYPE: DNA
<213> ORGANISM: Artificial Sequence
<220> FEATURE:
<223> OTHER INFORMATION: primer

<400> SEQUENCE: 14
taagtcttca atgtgactga ct                                              22

<210> SEQ ID NO 15
<211> LENGTH: 22
<212> TYPE: DNA
<213> ORGANISM: Artificial Sequence
<220> FEATURE:
<223> OTHER INFORMATION: primer

<400> SEQUENCE: 15
gactttagtt gctggtctta ca                                              22

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
gagctggtct cactcaaagc                                                 20

<210> SEQ ID NO 17
<211> LENGTH: 21
<212> TYPE: DNA
<213> ORGANISM: Artificial Sequence
<220> FEATURE:
<223> OTHER INFORMATION: primer

<400> SEQUENCE: 17
cagttgacag gcatgcttga t                                               21

<210> SEQ ID NO 18
<211> LENGTH: 30
<212> TYPE: DNA
<213> ORGANISM: Artificial Sequence
<220> FEATURE:
<223> OTHER INFORMATION: primer

<400> SEQUENCE: 18
cgagctgctc tatagactgc tgggtagtcc                                      30

<210> SEQ ID NO 19
<211> LENGTH: 30
<212> TYPE: DNA
<213> ORGANISM: Artificial Sequence
<220> FEATURE:
<223> OTHER INFORMATION: primer

<400> SEQUENCE: 19
taacagaggt ggcttatgag tatttcttcc                                      30

<210> SEQ ID NO 20
<211> LENGTH: 20
<212> TYPE: DNA
<213> ORGANISM: Artificial Sequence
<220> FEATURE:
<223> OTHER INFORMATION: primer

```
<400> SEQUENCE: 20
ggtggtatct gaaagtatcc                                              20

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
ggatactttc agataccacc                                              20

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
aggaggaagt agagcccggg                                              20

<210> SEQ ID NO 23
<211> LENGTH: 23
<212> TYPE: DNA
<213> ORGANISM: Artificial Sequence
<220> FEATURE:
<223> OTHER INFORMATION: primer

<400> SEQUENCE: 23
acattgaagc catccactac gaa                                          23

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
gttaggtcag attccagttc                                              20

<210> SEQ ID NO 25
<211> LENGTH: 30
<212> TYPE: DNA
<213> ORGANISM: Artificial Sequence
<220> FEATURE:
<223> OTHER INFORMATION: primer

<400> SEQUENCE: 25
ggcttgccct tgccctgctt gtgccgtgta                                   30

<210> SEQ ID NO 26
<211> LENGTH: 31
<212> TYPE: DNA
<213> ORGANISM: Artificial Sequence
<220> FEATURE:
<223> OTHER INFORMATION: primer

<400> SEQUENCE: 26
ccacagaggc agggcacgga gtttgtctgt g                                 31

<210> SEQ ID NO 27
<211> LENGTH: 4
```

```
<212> TYPE: PRT
<213> ORGANISM: Caspase cleavage site

<400> SEQUENCE: 27

Asp Asn Val Asp
1
```

GNK INTERACTING AMINO ACID DECARBOXYLASE AND METHODS OF USE THEREOF

CROSS-REFERENCE TO RELATED APPLICATIONS

The present Application is a non-provisional application claiming the priority of copending provisional U.S. Ser. No. 60/241,324, filed Oct. 18, 2000, the disclosure of which is hereby incorporated by reference in its entirety. Applicants claim the benefits of this Application under 35 U.S.C. §119(e).

FIELD OF THE INVENTION

The present invention relates generally to a novel polypeptide that contains an amino acid decarboxylase domain, has a consensus caspase-3 cleavage motif and is a substrate for caspase-3 in vitro. The present invention further relates to the nucleic acids that encode the novel polypeptide and the antibodies to the decarboxylase. Methods of using the novel polypeptides, nucleic acids and antibodies are also provided.

BACKGROUND OF THE INVENTION

GNK and sGNK: A Kinase and its Putative Polypeptide Substrate

The isolation of a novel protein kinase, GNK, has been recently disclosed [Sims et al., WO 97/47750]. GNK was originally identified as an IL-1 stimulated kinase and was initially named ITAK (IL-1/TNF-$\alpha$ activated Kinase). However, GNK, which is short for GEF containing NEK-like Kinase, was subsequently renamed for its structural/catalytic components, i.e., it contains both (i) an N-terminal kinase domain most similar to that of protein kinase Nek-2, and (ii) a domain that is homologous to the Guanine nucleotide Exchange Factor (GEF) family of proteins [U.S. Pat. No. 6,080,557, Issued Jun. 27, 2000, WO 97/47750, and WO 00/36097 the contents of which are hereby incorporated by reference in their entireties]. A polypeptide substrate for GNK, which was named sGNK, was found to co-purify with the protein kinase. Both GNK and sGNK appear to play a role in the regulation of vascularization during embryonic development.

GNK has an approximate molecular weight of 110 kDa, and is capable of phosphorylating polypeptide substrates such as sGNK, as well as undergoing autophosphorylation. Phosphorylated-GNK demonstrates a strong tendency to oligomerize. Based on SDS-PAGE and SUPERDEX 200 size exclusion chromatography analyses, phosphorylated-GNK forms trimers and also higher-order complexes.

As indicated above, GNK has both a kinase domain and a GEF-like domain. The kinase domain of GNK is most similar to the NIMA family of kinases, particularly Nek2 (NIMA-related kinase 2). The Nek2 kinase is a dual specificity kinase associated with regulation of the cell cycle. Nek2 associates with the centrosomes of all cells during all stages of the cell cycle and has been shown to be a bona fide component of the core centrosome [Fry et al., EMBO J. 17:470–481 (1998)]. GEF polypeptides are activators of the Ras superfamily of proteins [Overbeck et al., Mol. Repro. and Dev., 42:468, (1995)], which play a role in the regulation of a wide variety of cellular activities, such as cell proliferation and differentiation, cytoskeletal organization, nuclear transport, and the cell cycle. Ras superfamily proteins are GTP binding proteins which are active when bound to GTP, but become inactive when the GTP is hydrolyzed to GDP. GEFs positively regulate Ras activity by promoting the release of bound GDP, thereby facilitating GTP binding and Ras activation.

sGNK is approximately 90 kilodaltons (kDa), appears to have a high degree of coiled-coil structure, and appears to be the human homologue of the Drosophila bicaudal-D protein. sGNK also has a region of similarity with a newly discovered polypeptide, C-Nap1. Mutations in bicaudal-D disrupt the cytoskeleton, interfere with messenger RNA (mRNA) sorting, and disrupt the polarity of the developing Drosophila embryo [Baens and Marynen, Genomics, 45:601–606 (1997)]. C-Nap1 is a novel centrosomal coiled coil protein that appears to be the substrate of Nek2 [Fry et al., J. Cell Biol. 141:1563–1574 (1998)]. C-Nap1, like Nek2, is a core component of the human centrosome, that associates with centrosomes independently of the microtubules [Fry et al., J. Cell Biol. 141:1563–1574 (1998)]. C-Nap1 and Nek2 are known to co-localize in the centrosome and both have been detected in all cell types examined. A recent model suggests that C-Nap1 may function as part of the centrosomal "glue", by linking the ends of centrioles to each other during interphase. C-Nap1 is believed to be phosphorylated by Nek2 at the onset of mitosis, causing C-Nap1 to depolymerize or break down, which in turn permits the centrosomes to split during mitosis. Since sGNK is phosphorylated by GNK in vitro, the interaction between GNK and its substrate sGNK may resemble that observed with Nek2 and C-Nap1.

Decarboxylases

Decarboxylases are enzymes that catalyze the cleavage of the C—C bond between the $\alpha$-carbon atom and the carboxyl carbon atom of various amino acids. Aromatic L-amino acid decarboxylase (AADC) is one of the best characterized amino acid decarboxylases. AADC catalyzes the decarboxylation of L-dopa to dopamine and 5-hydroxytryptophan to serotonin. It also catalyzes the decarboxylation of tyrosine, tryptophan and phenylalanine to their corresponding amines. Whereas the role of AADC as a modulator of central neurotransmission is well-established, the function of non-neuronal forms of AADC is not understood. AADC activity is regulated by phosphorylation via a protein kinase A (PKA) dependent mechanism. Importantly, a number of peripheral cancers are characterized by unusually high AADC activity associated with the tumor. Large increases in AADC activity (i.e., relative to normal tissue levels) are seen in lung cancers of small cell origin as well as in primary small bowel cancer and its related metastases in spleen and liver. The significance of such increases in AADC activity is not understood. In contrast, several mouse neuroblastoma cell lines have little if any AADC activity. These observations suggest that the levels of AADC activity may be linked to cell survival.

Glutamic acid decarboxylase (GAD) is another well-characterized decarboxylase. GAD is responsible for production of the inhibitory neurotransmitter GABA ($\gamma$-amino butyric acid). Outside the central nervous system, GAD is also expressed in pancreatic islet cells, and one GAD isoform, GAD65, is a major target of autoimmune responses directed against pancreatic b cells in type I diabetes. GAD auto-antibodies can be detected years before the clinical onset of type I diabetes, and models for using GAD in a strategy to prevent diabetes have been reported. GAD has also been demonstrated to be the major antigen in the stiff man syndrome (SMS) a rare neurological disease in which GABA secreting neurons are thought to be affected.

Apoptosis

Cell death can occur by either necrosis or apoptosis. Whereas necrosis generally involves the simultaneous death of a group of juxtaposed cells due to circumstances that overwhelm/overcome the defenses/integrity of the cell, apoptosis is a highly regulated process that can occur in a single cell to (i) protect the surrounding cells and/or tissue, or (ii) remove unneeded cells, e.g., during embryonic development. Thus apoptosis has been aptly described as programmed cell death. Importantly, unlike necrosis, apoptosis does not lead to a strong immune response.

Caspases are a group of proteases that are known to play an important role in apoptosis. Caspases contain a cysteine residue in their active site and cleave their polypeptide substrates at aspartyl residues. One particular caspase, caspase-3 has been implicated as a downstream "executioner" in neuronal apoptosis [Beer et al., *J. Neurochem.* 75:1264–1273 (2000)]. Caspase-3 has also been shown to cleave the protein gelsolin in cells exposed to the apoptosis signaling protein Fas, with the resulting gelsolin fragments cleaving the actin filaments of the cell in a $Ca^{2+}$-dependent manner [Kothakota et al., *Science* 278:294–298 (1997)].

Therefore there is a need to identify additional polypeptides that interact with GNK and/or sGNK. In addition, there remains a need to identify alternative substrates for caspase-3. Furthermore, there is a need to provide additional assays for caspase-3.

The citation of any reference herein should not be construed as an admission that such reference is available as "Prior Art" to the instant application.

SUMMARY OF THE INVENTION

The present invention provides a novel polypeptide GNK Interacting Decarboxylase (GID) that comprises a decarboxylase domain, has a consensus caspase-3 cleavage motif and is a substrate for caspase-3 in vitro. The novel polypeptide is also a binding partner to the GNK protein kinase and the GNK protein kinase substrate, sGNK. Isolated nucleic acids encoding the GID polypeptide are also part of the present invention, as are antibodies to the GID polypeptide and fragments thereof. Furthermore, the present invention provides methods of using these polypeptides, polypeptide fragments, nucleic acids, and antibodies.

Therefore, the present invention provides a nucleic acid encoding a human GID that comprises the amino acid sequence of SEQ ID NO:2. In a preferred embodiment of this type, the isolated nucleic acid comprises the nucleotide sequence of SEQ ID NO:1. In a related embodiment, the nucleic acid encodes a GID that comprises the amino acid sequence of SEQ ID NO:2 comprising a conservative amino acid substitution. Preferably the nucleic acid encodes a GID that retains at least one, and more preferably at least two, and most preferably all of the following characteristics, i.e., (i) it catalyzes the decarboxylation of an amino acid, (ii) it is a substrate for caspase-3, (iii) it binds GNK, and/or (iv) it binds sGNK.

In still another embodiment the isolated nucleic acid encodes a fragment of a GID polypeptide. In a particular embodiment of this type the nucleic acid encodes a decarboxylase domain comprising the amino acid sequence of amino acids 216–395 of SEQ ID NO:2. In a related embodiment the nucleic acid encodes a decarboxylase domain that comprises the amino acid sequence of amino acids 216–395 of SEQ ID NO:2 having a conservative amino acid substitution. Preferably, this fragment retains decarboxylase activity. In still another embodiment, the nucleic acid encodes an antigenic fragment of GID. In yet another embodiment, the nucleic acid encodes a proteolytic fragment of GID that comprises at least 5, preferably at least 10 and more preferably at least 30 amino acid residues. In a particular embodiment, the nucleic acid encodes a proteolytic fragment produced by treating GID with caspase-3. In a preferred embodiment of this type, the nucleic acid encodes a caspase-3 fragment that is a 58 kilodalton fragment. In yet another embodiment, the nucleic acid encodes a fragment of GID that can bind to GNK. In still another embodiment the nucleic acid encodes a fragment of GID that can bind to sGNK.

The present invention also provides a modified GID in which the caspase-3 recognition motif (i.e., the cleavage site) has been modified such that it is no longer a substrate for caspase-3. Alterations/substitutions of one or more of the amino acid residues of the DNVD sequence (SEQ ID NO:27), and preferably of the second aspartic acid residue, results in such a modified GID. The resulting modified GID could be used as an inhibitor of caspase-3 in a cell, or as a control in a caspase-3 assay in which GID or a fragment thereof is used as the substrate.

All of the nucleic acids of the present invention can further comprise a heterologous nucleotide sequence. Furthermore, the present invention provides recombinant DNA molecules comprising the nucleic acids of the present invention that are operatively linked to an expression control sequence. In addition, the present invention also provides expression vectors that contain the recombinant DNA molecules of the present invention. Methods of expressing recombinant GID polypeptides and fragments in a cell containing an expression vector of the present invention are also included. One such method comprises culturing the cell in an appropriate cell culture medium under conditions that provide for expression of recombinant GID or GID fragment by the cell. In a preferred embodiment of this type, the method further comprises the step of purifying the recombinant GID or GID fragment. The purified form of the recombinant GID or GID fragment is also part of the present invention.

The present invention also provides a human GID that comprises the amino acid sequence of SEQ ID NO:2. In a related embodiment, the GID comprises the amino acid sequence of SEQ ID NO:2 comprising a conservative amino acid substitution. Preferably the GID retains at least one, and more preferably at least two and most preferably all of the following characteristics, i.e., (i) it catalyzes the decarboxylation of an amino acid, (ii) it is a substrate for caspase-3, (iii) it binds GNK, and/or (iv) it binds sGNK.

The present invention further provides fragments of a GID polypeptide. In a particular embodiment of this type the fragment comprises the decarboxylase domain comprising the amino acid sequence of amino acids 216–395 of SEQ ID NO:2. In a related embodiment the fragment comprises the decarboxylase domain comprising the amino acid sequence of amino acids 216–395 of SEQ ID NO:2 having a conservative amino acid substitution. Preferably, this fragment retains decarboxylase activity. In still another embodiment, the fragment is an antigenic fragment of GID. In yet another embodiment, the fragment is a proteolytic fragment of GID that comprises at least 5, preferably at least 10 and more preferably at least 30 amino acid residues. In a particular embodiment, the proteolytic fragment is produced by treating GID with caspase-3. In a preferred embodiment of this type, the caspase-3 fragment is a 58 kilodalton fragment. In yet another embodiment, the fragment of GID can bind to GNK. In still another embodiment the fragment of GID can bind to sGNK. The present invention also provides chimeric and/or fusion proteins that comprise the GID polypeptides and fragments of the present invention.

In addition, the present invention provides antibodies to the isolated GID polypeptides and fragments of the present invention. In a particular embodiment the antibody is a polyclonal antibody. In another embodiment the antibody is a monoclonal antibody. In yet another embodiment the antibody is a chimeric antibody. In a particular embodiment of this type, the antibody is a humanized antibody. The present invention further provides an immortal cell line that produces a monoclonal or chimeric antibody of the present invention.

The present invention further provides methods of isolating GNK and/or sGNK from a sample, preferably a mammalian cell and/or tissue sample, using GID or a fragment of GID that binds either sGNK or GNK. One such method comprises preparing an extract of a mammalian tissue sample and then passing the sample over a solid support (e.g., a column) that comprises GID or a fragment of GID that binds GNK and/or sGNK, under conditions in which GNK and/or sGNK bind to the solid support. The solid support is then washed to remove constituents of the extract that bind to the solid support in a non-specific manner. Finally, GNK and/or sGNK are eluted from the solid support, resulting in their isolation from the mammalian tissue sample. The solid support comprising GID or a fragment of GID that binds GNK and/or sGNK is also part of the present invention.

The present invention further provides methods of determining whether a sample, preferably a mammalian cell and/or tissue sample contains caspase-3. One such embodiment comprises preparing an extract of the mammalian cell or tissue sample and contacting the extract with GID. It is then determined whether the GID is cleaved by caspase-3 by determining whether cleavage products of the GID are detected. In a particular embodiment, caspase-3 cleaves GID into two distinct products and the detection of the two distinct cleavage products is assayed. In another embodiment, the detection of a 58 kilodalton fragment of GID is assayed. In a particular embodiment, antibodies specific for the caspase-3 cleavage products are used in the detection step. The cleavage products and the corresponding antibodies are also part of the present invention.

These and other aspects of the present invention will be better appreciated by reference to the following drawings and Detailed Description.

DETAILED DESCRIPTION OF THE INVENTION

Figure 1:
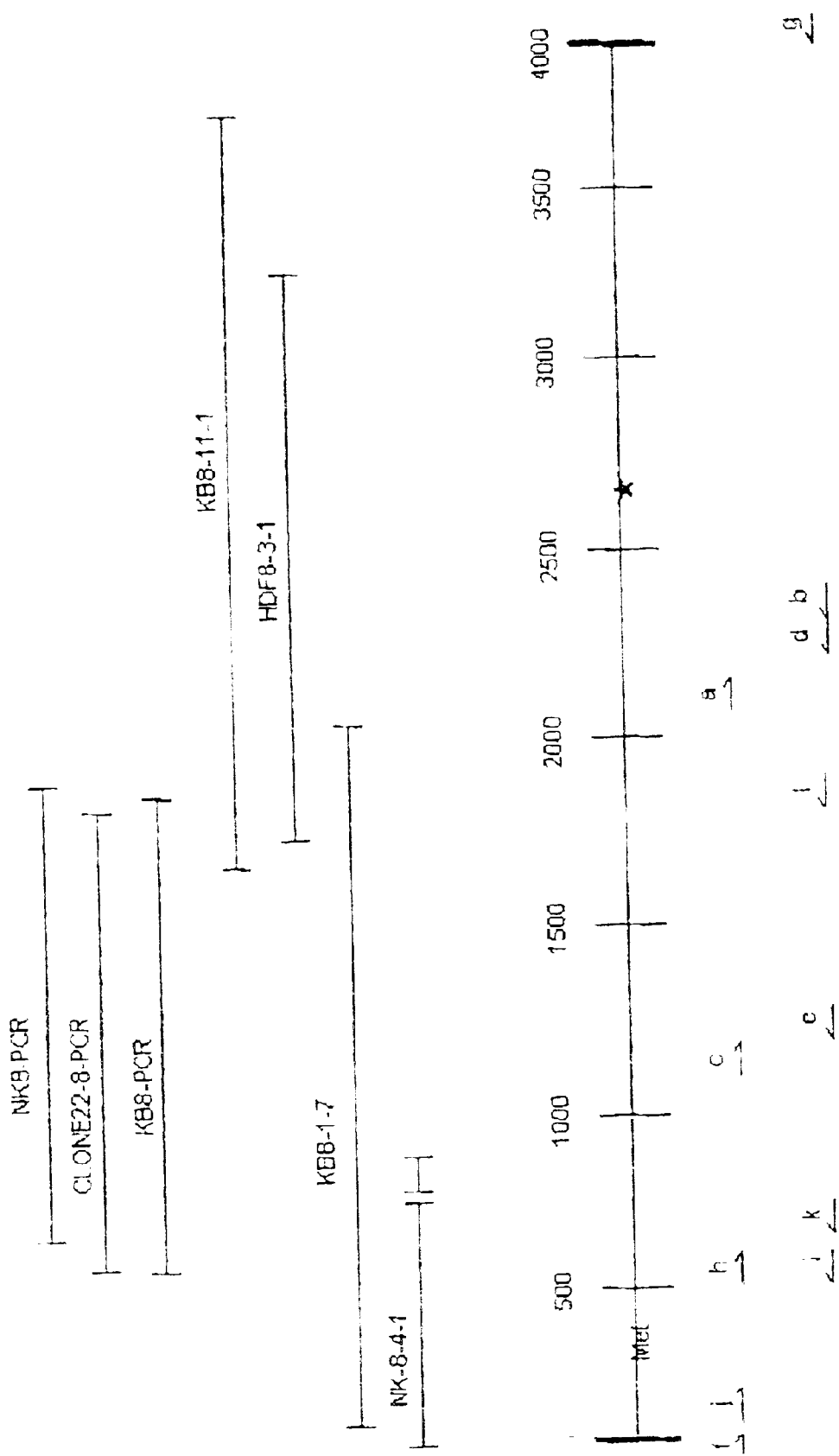
FIG. 1 is a schematic diagram depicting the relative positions of the cDNA clones used to construct the full length cDNA encoding GID.

The present invention provides a cDNA encoding a novel 788 amino acid polypeptide, GNK Interacting Decarboxylase (GID), that co-purifies with the polypeptides GNK and sGNK. Co-purification of GID with sGNK and GNK indicates that these three distinct polypeptides are components of a multi-protein complex. The GID polypeptide is also provided by the present invention, as is the multi-protein complex. The present invention further provides antibodies to GID, including humanized antibodies, as well as chimeric and fusion proteins comprising GID. In addition, methods of using these compositions in assays measuring caspase-3 activity are also provided.

The nucleotide sequence of GID was obtained by designing oligonucleotide probes based on tryptic digested peptide sequences to screen various cDNA libraries (see Example below). A composite nucleotide sequence for GID was derived from independent clones from KB and dermal fibroblast libraries. Sequence analysis of GID by scanning public databases for related polypeptides reveals that the central portion of GID has homology with the amino acid decarboxylase gene family. Alignment of members of this gene family from a variety of species shows a number of invariant or conservatively substituted residues within a region of roughly 200 amino acids. Mutagenesis studies have indicated that several of these residues are required for decarboxylase activity. GID contains most but not all of these residues (see alignment). Given the relatedness of GID to AADC and GAD, it is likely that expression of GID is also altered in certain cancers and/or disease states. GID contains a C-terminal coiled-coil domain of roughly 40 amino acids at position 585–631. Coiled-coil regions are predicted to be involved in protein-protein interactions. Immediately upstream of the coiled-coil region lies the sequence DNVD (SEQ ID NO:27) which corresponds to a potential consensus caspase recognition site. Incubation of in vitro translated $^{35}$S-labeled GID with caspase-3 results in the generation of a 58 kDa fragment. This cleavage pattern is consistent with the predicted fragment size when cleavage occurs at the DNVD sequence, thereby liberating the catalytic portion of GID from its coiled-coil domain.

Cleavage of caspase substrates can either stimulate or abolish their enzymatic activity, and strongly suggests that these events play important roles in the initiation and progression of apoptosis. The identification of caspase substrates is critical in understanding how these proteases induce the phenotypes associated with programmed cell death. The cleavage of GID by caspase-3 in vitro further supports the idea that GID activity may have important roles in promoting cell survival. Expression of GNK and GID in 293 Ebna cells demonstrates that these polypeptides can associate with one another. Immunoprecipitated GNK analyzed by Western blotting for the presence of any associated polypeptides indicates that GID is capable of binding GNK, further supporting the determination that GNK, sGNK and GID are components of a multi-protein complex.

Thus, GID is a decarboxylase for specific amino acids which are likely to play a role in cellular metabolism or function, as GID itself is an in vitro substrate for caspase-3, an inducer of apoptosis. Thus, the regulation of GID may be important in a wide variety of physiological processes. In a manner similar to other decarboxylases, its dysregulation may contribute to the pathogenesis of many diseases including cancer, autoimmunity, and neurodegenerative disorders. Altered expression of GID could serve as a marker for various disease states. Similarly, cleavage of GID may serve as a marker for cells undergoing apoptosis.

The association of GID with GNK and sGNK suggests that these polypeptides may function coordinately in specific cellular processes. As GNK is likely to play a role in vascular development and can associate with GID, GID may also contribute to proper formation and maintenance of the vasculature.

```
                GID Nucleic Acid Sequence (SEQ ID NO:1):

1 ATGGACGCGT CCCTGGAGAA GATAGCAGAC CCCACGTTAG CTGAAATGGG

51 AAAAAACTTG AAGGAGGCAG TGAAGATGCT GGAGGACAGT CAGAGAAGAA

101 CAGAAGAGGA AAATGGAAAG AAGCTCATAT CCGGAGATAT TCCAGGCCCA

151 CTCCAGGGCA GTGGGCAAGA TATGGTGAGC ATCCTCCAGT TAGTTCAGAA

201 TCTCATGCAT GGAGATGAAG ATGAGGAGCC CCAGAGCCCC AGAATCCAAA

251 ATATTGGAGA ACAAGGTCAT ATGGCTTTGT TGGGACATAG TCTGGGAGCT

301 TATATTTCAA CTCTGGACAA AGAGAAGCTG AGAAAACTTA CAACTAGGAT

351 ACTTTCAGAT ACCACCTTAT GGCTATGCAG AATTTTCAGA TATGAAAATG

401 GGTGTGCTTA TTTCCACGAA GAGGAAAGAG AAGGACTTGC AAAGATATGT

451 AGGCTTGCCA TTCATTCTCG ATATGAAGAC TTCGTAGTGG ATGGCTTCAA

501 TGTGTTATAT AACAAGAAGC CTGTCATATA TCTTAGTGCT GCTGCTAGAC

551 CTGGCCTGGG CCAATACCTT TGTAATCAGC TCGGCTTGCC CTTCCCCTGC

601 TTGTGCCGTG TACCCTGTAA CACTGTGTTT GGATCCCAGC ATCAGATGGA

651 TGTTGCCTTC CTGGAGAAAC TGATTAAAGA TGATATAGAG CGAGGAAGAC

701 TGCCCCTGTT GCTTGTCGCA AATGCAGGAA CGGCAGCAGT AGGACACACA

751 GACAAGATTG GGAGATTGAA AGAACTCTGT GAGCAGTATG GCATATGGCT

801 TCATGTGGAG GGTGTGAATC TGGCAACATT GGCTCTGGGT TATGTCTCCT

851 CATCAGTGCT GGCTGCAGCC AAATGTGATA GCATGACGAT GACTCCTGGC

901 CCGTGGCTGG GTTTGCCAGC TGTTCCTGCG GTGACACTGT ATAAACACGA

951 TGACCCTGCC TTGACTTTAG TTGCTGGTCT TACATCAAAT AAGCCCACAG

1001 ACAAACTCCG TGCCCTGCCT CTGTGGTTAT CTTTACAATA CTTGGGACTT

1051 GATGGGTTTG TGGAGAGGAT CAAGCATGCC TGTCAACTGA GTCAACGGTT

1101 GCAGGAAAGT TTGAAGAAAG TGAATTACAT CAAAATCTTG GTGGAAGATG

1151 AGCTCAGCTC CCCAGTGGTG GTGTTCAGAT TTTTCCAGGA ATTACCAGGC

1201 TCAGATCCGG TGTTTAAAGC CGTCCCAGTG CCCAACATGA CACCTTCAGG
```

-continued
GID Nucleic Acid Sequence (SEQ ID NO:1):
1251 AGTCGGCCGG GAGAGGCACT CGTGTGACGC GCTGAATCGC TGGCTGGGAG

1301 AACAGCTGAA GCAGCTGGTG CCTGCAAGCG GCCTCACAGT CATGGATCTG

1351 GAAGCTGAGG GCACGTGTTT GCGGTTCAGC CCTTTGATGA CCGCAGCAGT

1401 TTTAGGAACT CGGGGAGAGG ATGTGGATCA GCTCGTAGCC TGCATAGAAA

1451 GCAAACTGCC AGTGCTGTGC TGTACGCTCC AGTTGCGTGA AGAGTTCAAG

1501 CAGGAAGTGG AAGCAACAGC AGGTCTCCTA TATGTTGATG ACCCTAACTG

1551 GTCTGGAATA GGGGTTGTCA GGTATGAACA TGCTAATGAT GATAAGAGCA

1601 GTTTGAAATC AGATCCCGAA GGGGAAAACA TCCATGCTGG ACTCCTGAAG

1651 AAGTTAAATG AACTGGAATC TGACCTAACC TTTAAAATAG GCCCTGAGTA

1701 TAAGAGCATG AAGAGCTGCC TTTATGTCGG CATGGCGAGC GACAACGTCG

1751 ATGCTGCTGA GCTCGTGGAG ACCATTGCGG CCACAGCCCG GGAGATAGAG

1801 GAGAACTCGA GGCTTCTGGA AAACATGACA GAAGTGGTTC GGAAAGGCAT

1851 TCAGGAAGCT CAAGTGGAGC TGCAGAAGGC AAGTGAAGAA CGGCTTCTGG

1901 AAGAGGGGGT GTTGCGGCAG ATCCCTGTAG TGGGCTCCGT GCTGAATTGG

1951 TTTTCTCCGG TCCAGGCTTT ACAGAAGGGA AGAACTTTTA ACTTGACAGC

2001 AGGCTCTCTG GAGTCCACAG AACCCATATA TGTCTACAAA GCACAAGGTG

2051 CAGGAGTCAC GCTGCCTCCA ACGCCCTCGG GCAGTCGCAC CAAGCAGAGG

2101 CTTCCAGGCC AGAAGCCTTT TAAAAGGTCC CTGCGAGGTT CAGATGCTTT

2151 GAGTGAGACC AGCTCAGTCA GTCACATTGA AGACTTAGAA AAGGTGGAGC

2201 GCCTATCCAG TGGGCCGGAG CAGATCACCC TCGAGGCCAG CAGCACTGAG

2251 GGACACCCAG GGGCTCCCAG CCCTCAGCAC ACCGACCAGA CCGAGGCCTT

2301 CCAGAAAGGG GTCCCACACC CAGAAGATGA CCACTCACAG GTAGAAGGAC

2351 CGGAGAGCTT AAGATGA

1 MDASLEKIAD PTLAEMGKNL KEAVKMLEDS QRRTEEENGK KLISGDIPGP

51 LQGSGQDMVS ILQLVQNLMH GDEDEEPQSP RIQNIGEQGH MALLGHSLGA

101 YISTLDKEKL RKLTTRILSD TTLWLCRIFR YENGCAYFHE EEREGLAKIC

151 RLAIHSRYED FVVDGFNVLY NKKPVIYLSA AARPGLGQYL CNQLGLPFPC

201 LCRVPCNTVF GSQHQMDVAF LEKLIKDDIE RGRLPLLLVA NAGTAAVGHT

251 DKIGRLKELC EQYGIWLHVE GVNLATLALG YVSSSVLAAA KCDSMTMTPG

301 PWLGLPAVPA VTLYKHDDPA LTLVAGLTSN KPTDKLRALP LWLSLQYLGL

351 DGFVERIKHA CQLSQRLQES LKKVNYIKIL VEDELSSPVV VFRFFQELPG

401 SDPVFKAVPV PNMTPSGVGR ERHSCDALNR WLGEQLKQLV PASGLTVMDL

451 EAEGTCLRFS PLMTAAVLGT RGEDVDQLVA CIESKLPVLC CTLQLREEFK

501 QEVEATAGLL YVDDPNWSGI GVVRYEHAND DKSSLKSDPE GENIHAGLLK

551 KLNELESDLT FKIGPEYKSM KSCLYVGMAS DNVDAAELVE TIAATAREIE

601 ENSRLLENMT EVVRKGIQEA QVELQKASEE RLLEEGVLRQ IPVVGSVLNW

651 FSPVQALQKG RTFNLTAGSL ESTEPIYVYK AQGAGVTLPP TPSGSRTKQR

701 LPGQKPFKRS LRGSDALSET SSVSHIEDLE KVERLSSGPE QITLEASSTE

751 GHPGAPSPQH TDQTEAFQKG VPHPEDDHSQ VEGPESLR

```
                                                                              SEQ ID NO:
periTDC       G....KLVCY  GSDQTHTMFP  KTCKLAGIYP  NNIRLIPTTV  ETDFGISPQV        3
tdc           H....KLVVY  GSDQTHSTYA  KACNLAGILP  CNIRSIRTEA  VANFSLSPDS        4
arabYDC       E....KLVVY  SSDQTHSALQ  KACQIAGIHP  ENCRVLTTDS  STNYALRPES        5
hUHDC         A....RLVAY  ASDQAHSSVE  KAGLISLV..  .KMKFLPVD.  .DNFSLRGEA        6
ratHDC        A....RLVAY  ASDQAHSSVE  KAGLISLV..  .KIKFLPVD.  .DNFSLRGEA        7
ratAAD        E....RLVAY  TSDQAHSSVE  RAGLIGV...  .KIKAIPSD.  .GNYSMRAAA        8
GAD6S         .AAVPRLIAF  TSEHSHFSLK  KGAAALGIGT  DSVILIKCDE  RGK..MIPSD        9
drosGAD       .FNAKPLIIF  TSEDAHYSVE  KLMAFMGFGS  DHVRKIATNE  VGK..MRLSD       10
dabdc         AEAMKNVKVI  CSENAHFSVQ  KNMAMMGMGF  QSVVTVPVNE  NAQ..MDVDA       11
Band8cregio   ~~~~~~~~~~  ~~~~~~~~~~  ~~~~~~~~~~  ~~~~~~~~~~  ~~~~~~MDVAF      12 periTDC       LRKMVEDDVA  AGYVPLFLCA  TLGTTSTTAT  DPVDSLSEIA  NEFGIWIHVD        3
tdc           LHREIEADVA  AGMVPLYLCA  TVGTTSTTAI  DSLSPLADVA  NDYGLWFHVD        4
arabYDC       LQEAVSRDLE  AGLIPFFLCA  NVGTTSSTAV  DPLAALGKIA  NSNDIWFHVD        5
huHDC         LQKAIEEDKQ  RGLVPVFVCA  TLGTTGVCAF  DCLSELGPIC  AREGLWLHID        6
ratHDC        LQKAIEEDKQ  QGLVPVFVCA  TLGTTGVCAF  DKLSELGPIC  AREGLWLHVD        7
ratAADC       LREALERDKA  AGLIPFFVVV  TLGTTSCCSF  DNLLEVGPIC  NQEGVWLHID        8
GAD65         LERRILEAKQ  KGFVPFLVSA  TAGTTVYGAF  DPLLAVADIC  KKYKIWMHVD        9
drosGAD       LEKQVKLCLE  NGWQPLMVSA  TAGTTVLGAF  DDLAGISEVC  KKYNMWMHVD       10
dabdc         LEKTMAHLQA  EGKVVACVVA  TAGTTDAGAI  HPLKKIREIT  NKYGSWMHID       11
Band8dcregio  LEKLIKDDIE  RGRLPLLLVA  NAGTAAVGHT  DKIGRLKELC  EQYGIWLHVE       12
                  *         *  *  *       **       *               *  ** periTDC       AAYAGSACIC  PEFRHYLDGI  ERVDSLSLSP  HKWL.LAYLD  CTCLWVKQPH        3
tdc           AAYAGSACIC  PEFRHYLDGI  ERADSLSLSP  HKWL.LSYLD  CCCLWVKRPS        4
arabYDC       AAYAGSACIC  PEYRQYIDGV  ETADSFNMNA  HKWF.LTNFD  CSLLWVKDQD        5
huHDC         AAYAGTAFLC  PEFRGFLKGI  EYADSFTFNP  SKWM.MVHFD  CTGFWVKDKY        6
ratHDC        AAYAGTAFLR  PELRGFLKGI  EYADSFTFNP  SKWM.MVHFD  CTGFWVKDKY        7
ratAADC       AAYAGSAFIC  PEFRYLLNGV  EFADSFNFNP  HKWL.LVNFD  CSAMWVKKRT        8
GAD65         AAWGGGLLMS  RKHKWKLSGV  ERANSVTWNP  HKMM.GVPLQ  CSALLVREEG        9
drosGAD       AAWGGGLMS   KKYRHLLNGI  ERADSVTWNP  HKLL.AASQQ  CSTFLTRHQQ       10
dabdc         AAWGGALILS  NTYRAMLDGI  ELSDSITLDF  HKHY.FQSIS  CGAFLLKDEA       11
Band8dcregio  GVNLATLADG  YVSSSVLAAA  K.CDSMTMTP  GPWLGLPAVP  AVTLYKHDDP       12
                              *              **      * periTDC       LLLRALTTNP  EYL..KNKQS  DLDKVV.DFK  NWQIATGRKF  RSLKLWLILR        3
tdc           VLVKALSTDP  EYL..KNKPS  ESNSVV.DFK  DWQVGTGRRF  KALRLWFVMR        4
arabYDC       SLTLALSTNP  EFL..KNKAS  QANLVV.DYK  DWQIPLGRRF  RSLKLWMVLR        5
huHDC         KLQQTFSVNP  IYL..RHA..  NSGVAT.DFM  HWQIPLSRRF  RSVKLWFVIR        6
ratHDC        KLQQTFSVNP  IYL..RHA..  NSGVAT.DFM  HWQIPLSRRF  RSIKLWFVIR        7
ratAADC       DLTEAFNMDP  VYL..RHSHQ  DSGLIT.DYR  HWQIPLGRRF  RSLKMWFVFR        8
GAD65         LMQSCNQMHA  SYLFQQDKHY  DLSYDTGD..  .KALQCGRHV  DVFKLWLMWR        9
drosGAD       VLAQCHSTNA  TYLFQKDKFY  DTSFDTGD..  .KHIQCGRRA  DVFKFWFMWK       10
dabdc         NYRFMH.YEA  EYL...NSAY  DEEHGVPNLV  SKSLQTTRRF  DALKLWMTIE       11
Band8dcregio  ALTLVAGL..  ....TSNKPT  D.........  ........KL  RALPLWLSLQ       12
                  *                                              ** periTDC       SYGVVNLQSH  IRSDVAMGKM  FEEWVRSDSR  FEIVVPRN..  FSLVCFRLKP        3
tdc           SYGVANLQSH  IRSDIQMAKM  FEEFVNSDPR  FEIVVPRV..  FSLVCFRLNP        4
arabYDC       LYGSETLKSY  IRNHIKLAKE  FEQLVSQDPN  FEIVTPRI..  FALVCFRLVP        5
huHDC         SFGVKNLQAH  VRHGTEMAKY  FESLVRNDPS  FEIPAKRH..  LGLVVFRLK.        6
ratHDC        SFGVKNLQAH  VRHGTDMAKY  FESLVRSDPV  FEIPAERH..  LGLVVFRLK.        7
ratAADC       MYGVKGLQAY  IRKHVKLSHE  FESLVRQDPR  FEICTEVI..  LGLVCFFRLK        8
GAD65         AKGTTGFEAH  IDKCLELAEY  LYNIIKNREG  YEMVFDGKPQ  HTNVCFWYVP        9
drosGAD       AKGTQGLEAH  VEKVFRMAEF  FTAKVRERPG  FELVLE.SPE  CTNISFWYVP       10
dabdc         SLGEELYGSM  IDHGVKLTRE  VADYIKATEG  LELLVE..PQ  FASVLFRVVP       11
Band8dcregio  YLGLDGFVER  IKHACQLSQR  LQESLKKVNY  IKILVEDELS  SPVVVFRFFQ       12
                  *                                              *  *
``` periTDC:      tryptophan decarboxylase, Periwinkle Acc#P17770
tdc:          tryptophan decarboxylase, Camptotheca acuminata, Acc#U73657
arabYDC:      tyrosine decarboxylase, Arabidopsis thaliana Acc#AAD21754
huHDC:        histidine decarboxylase, Human, Acc#P19113
ratHDC:       histidine decarboxylase, Rat, Acc#P16453
GADG5:        glutamate decarboxylase, Rat, Acc#M72422
DrosGAD:      glutamate decarboxylase, Drosophila melanogaster, Acc#JH0827
dabdc:        L-2,4 diaminobutyrate decarboxylase, Acinetobacter baumannii, Acc#55724
Band8dcregion,GID: decarboxylase homology region, amino acids 216–395.

Therefore, if appearing herein, the following terms shall have the definitions set out below.

As used herein comprising a "biological activity" of a GID means comprising one or more of the biological activities of GID which includes:

(1) amino acid decarboxylation;
(2) being a substrate for caspase-3;
(3) binding GNK; and
(4) binding sGNK.

As used herein a "biologically active" GID polypeptide is a polypeptide that retains at least one biological activity of the native GID polypeptide. Biological activity includes, inter alia, amino acid decarboxylase activity, the ability to be cleaved by caspase-3, and the ability to bind GNK and/or bind sGNK.

As used herein the terms "fusion protein" and "fusion peptide" are used interchangeably and encompass "chimeric proteins and/or chimeric peptides" and fusion "intein proteins/peptides". A GID fusion protein of the present invention comprises at least a portion of a GID polypeptide of the present invention joined via a peptide bond to at least a portion of another protein or peptide. In a particular embodiment the portion of the GID is antigenic. For example fusion proteins can comprise a marker protein or peptide, or a protein or peptide that aids in the isolation and/or purification of a GID of the present invention.

A molecule is "antigenic" when it is capable of specifically interacting with an antigen recognition molecule of the immune system, such as an immunoglobulin (antibody) or T cell antigen receptor. An antigenic polypeptide contains at least about 5, and preferably at least about 10 or more amino acids. An antigenic portion of a molecule can be that portion that is immunodominant for antibody or T cell receptor recognition, or it can be a portion used to generate an antibody to the molecule by conjugating the antigenic portion to a carrier molecule for immunization. A molecule that is antigenic need not be itself immunogenic, i.e., capable of eliciting an immune response without a carrier.

As used herein the terms "approximately" and "about" are used to signify that a value is within twenty percent of the indicated value i.e., a polypeptide fragment containing "approximately" 150 amino acid residues can contain between 120 and 180 amino acid residues.

As used herein a "small organic molecule" is an organic compound [or organic compound complexed with an inorganic compound (e.g., metal)] that has a molecular weight of less than 3 kilodaltons.

As used herein a polypeptide or peptide "consisting essentially of" or that "consists essentially of" a specified amino acid sequence is a polypeptide or peptide that retains the general characteristics, e.g., activity of the polypeptide or peptide having the specified amino acid sequence and is otherwise identical to that polypeptide in amino acid sequence except it consists of plus or minus 5% or fewer, and preferably plus or minus 2.5% or fewer amino acid residues. Thus, a polypeptide that consists essentially of an amino acid sequence of SEQ ID NO:2 consists of between 749 to 827, and preferably 768 to 808 amino acid residues. Preferably the additional/missing amino acid residues are at or near the C-terminal or N-terminal portion of the polypeptide.

As used herein the term "binds to" is meant to include all such specific interactions that result in two or more molecules showing a preference for one another relative to some third molecule. This includes processes such as covalent, ionic, hydrophobic and hydrogen bonding but does not include non-specific associations such as solvent preferences.

As used herein, the term "homologue" is used interchangeably with the term "ortholog" and refers to the relationship between polypeptides that have a common evolutionary origin and differ because they originate from different species. For example, rabbit GID is a homologue of human GID.

Nucleic Acids Encoding GID

The present invention contemplates isolation of a nucleic acid encoding a vertebrate GID, including a full length, or naturally occurring form of GID from any species, preferably an animal, and more particularly a mammalian source. A nucleic acid encoding a human GID (hGID) is exemplified below.

In accordance with the present invention there may be employed conventional molecular biology, microbiology, and recombinant DNA techniques within the skill of the art. Such techniques are explained fully in the literature. [See, e.g., Sambrook, Fritsch & Maniatis, *Molecular Cloning: A Laboratory Manual,* Second Edition (1989) Cold Spring Harbor Laboratory Press, Cold Spring Harbor, N.Y. (herein "Sambrook et al., 1989"); *DNA Cloning: A Practical Approach,* Volumes I and II D. N. Glover ed. 1985; *Oligonucleotide Synthesis,* M. J. Gait ed. (1984); *Nucleic Acid Hybridization,* B. D. Hames & S. J. Higgins eds. (1985); *Transcription And Translation,* B. D. Hames & S. J. Higgins, eds. (1984); *Animal Cell Culture.* R. I. Freshney, ed. (1986); *Immobilized Cells And Enzymes,* IRL Press, (1986); B. Perbal, *A Practical Guide To Molecular Cloning* (1984); F. M. Ausubel et al. (eds.), *Current Protocols in Molecular Biology,* John Wiley & Sons, Inc. (1994)]. Therefore, if appearing herein, the following terms shall have the definitions set out below.

As used herein, the term "gene" refers to an assembly of nucleotides that encodes a polypeptide, and includes cDNA and genomic DNA nucleic acids. A nucleic acid encoding a GID of the present invention is not used herein as a synonym of the corresponding naturally occurring gene which contains all of the introns and regulatory sequences, e.g., promoters, present in the natural genomic DNA. Rather, a nucleic acid encoding a particular polypeptide can minimally contain just the corresponding coding nucleotide sequence for the polypeptide. In a particular embodiment, the nucleic acid does not contain at least one of the introns or regulatory sequences of the corresponding gene.

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell. A cell has been "transformed" by exogenous or heterologous DNA when the transfected DNA effects a phenotypic change. Preferably, the transforming DNA should be integrated (covalently linked) into chromosomal DNA making up the genome of the cell.

"Heterologous" DNA refers to DNA not naturally located in the cell, or in a chromosomal site of the cell. Preferably, the heterologous DNA includes a gene foreign to the cell.

A "heterologous nucleotide sequence" as used herein is a nucleotide sequence that is added to a nucleotide sequence of the present invention by recombinant methods to form a nucleic acid which is not naturally formed in nature. Such nucleic acids can encode chimeric and/or fusion proteins. Thus the heterologous nucleotide sequence can encode peptides and/or polypeptides which contain regulatory and/or structural properties. In another such embodiment the heterologous nucleotide can encode a polypeptide or peptide that functions as a means of detecting the polypeptide or peptide encoded by the nucleotide sequence of the present invention after the recombinant nucleic acid is expressed. In still another such embodiment the heterologous nucleotide can function as a means of detecting a nucleotide sequence of the present invention. A heterologous nucleotide sequence can comprise non-coding sequences including restriction sites, regulatory sites, promoters and the like.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA—DNA, DNA-RNA and RNA—RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5 prime to 3 prime direction along the non-transcribed strand of DNA (i.e., the strand having a sequence homologous to the mRNA). However, unless specifically stated otherwise, a designation of a nucleic acid includes both the non-transcribed strand referred to above, and its corresponding complementary strand. Such designations include SEQ ID NOs:. A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55° C., can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SSC. High stringency hybridization conditions correspond to the highest $T_m$, e.g., 50% formamide, 5× or 6×SSC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–10.51). For hybridization with shorter nucleic acids, i.e., oligonucleotides, the position of mismatches becomes more important, and the length of the oligonucleotide determines its specificity (see Sambrook et al., supra, 11.7–11.8). Preferably a minimum length for a hybridizable nucleic acid is at least about 12 nucleotides; preferably at least about 16 nucleotides; and more preferably the length is at least about 24 nucleotides; and most preferably at least 36 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C.

"Homologous recombination" refers to the insertion of a foreign DNA sequence of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5 prime (amino) terminus and a translation stop codon at the 3 prime (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3 prime to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter" is a DNA regulatory region capable of binding RNA polymerase in a cell and initiating transcription of a downstream (3 prime direction) coding sequence. For purposes of defining the present invention, the promoter is bounded at its 3 prime terminus by the transcription initiation site and extends upstream (5 prime direction) to include the minimum number of bases or elements necessary to initiate transcription at levels detectable above background. Within the promoter will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the polypeptide encoded by the coding sequence.

A "signal sequence" is included at the beginning of the coding sequence of a polypeptide to be expressed on the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of polypeptides native to eukaryotes and prokaryotes, and are often functional in both types of organisms.

The present invention encompasses nucleic acids that are substantially homologous to SEQ ID NO:1 and fragments thereof, and polypeptides that are substantially homologous to SEQ ID NO:2 and fragments thereof. Two nucleic acids are "substantially homologous" when their nucleotide sequences are at least 70%, preferably 80% or 90%, and more preferably 95%, 98%, or 99% identical. Similarly, two polypeptides are "substantially homologous" when their amino acid sequences are at least 70%, preferably 80% or 90%, and more preferably 95%, 98%, or 99% identical.

Percent identity, in the case of both polypeptides and nucleic acids, may be determined by visual inspection and mathematical calculation. Percent identity may also be determined using the alignment method of Needleman and Wunsch [*J. Mol. Biol.* 48:443, (1970), as revised by Smith and Waterman [*Adv. Appl. Math* 2:482, (1981)]. Preferably, percent identity is determined by using a computer program, for example, the GAP computer program version 10.x available from the Genetics Computer Group (GCG; Madison, Wis., see also Devereux et al., *Nucl. Acids Res.* 12:387, (1984)]. The preferred default parameters for the GAP program include: (1) a unary comparison matrix (containing a value of 1 for identities and 0 for non-identities) for nucleotides, and the weighted comparison matrix of Gribskov and Burgess, [*Nucl. Acids Res.* 14:6745, (1986)], as described by Schwartz and Dayhoff, eds., *Atlas of Protein Sequence and Structure,* National Biomedical Research Foundation, pp. 353–358, (1979) for amino acids; (2) a penalty of 30 (amino acids) or 50 (nucleotides) for each gap and an additional 1 (amino acids) or 3 (nucleotides) penalty for each symbol in each gap; (3) no penalty for end gaps; and (4) no maximum penalty for long gaps. Percent identity may also be determined using other programs known to those having ordinary skill in the art of sequence comparison. In the case of fragments of polypeptides or nucleic acids, percent identity is calculated based on the portion of GID polypeptide or nucleic acid that is present in the fragment.

The term "corresponding to" is used herein to refer to similar or homologous sequences, whether the exact position is identical or different from the molecule to which the similarity or homology is measured. Thus, the term "corresponding to" refers to the sequence similarity over a given sequence range (e.g. 50 nucleotides), and not the numbering of the amino acid residues or nucleotide bases.

A gene encoding a GID polypeptide, whether genomic DNA or cDNA, can be isolated from any source, particularly from a human cDNA or genomic library. Methods for obtaining a GID gene with the nucleotide information disclosed herein is well known in the art [see, e.g., Sambrook et al., 1989, supra].

Accordingly, any animal cell potentially can serve as the nucleic acid source for the molecular cloning of a GID gene. The DNA may be obtained by standard procedures known in the art from cloned DNA (e.g., a DNA "library"), by chemical synthesis, by cDNA cloning, or by the cloning of genomic DNA, or fragments thereof, purified from the desired cell [see, for example, Sambrook et al., 1989, supra; Glover, D. M. (ed.), 1985, DNA Cloning: A Practical Approach, MRL Press, Ltd., Oxford, U.K. Vol. I, II]. Clones derived from genomic DNA may contain regulatory and intron DNA regions in addition to coding regions; clones derived from cDNA will not contain intron sequences. Whatever the source, the gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired GID gene may be accomplished in a number of ways. For example, if an amount of a portion of a GID gene or its specific RNA, or a fragment thereof, is available and can be purified and labeled, the generated DNA fragments may be screened by nucleic acid hybridization to the labeled probe [Benton and Davis, *Science,* 196:180 (1977); Grunstein and Hogness, *Proc. Natl. Acad. Sci. U.S.A.,* 72:3961 (1975)]. For example, a set of oligonucleotides corresponding to the partial amino acid sequence information obtained for the GID polypeptide can be prepared and used as probes for DNA encoding a GID. Preferably, a fragment is selected that is highly unique to a GID. Those DNA fragments with substantial homology to the probe will hybridize. As noted above, the greater the degree of homology, the more stringent hybridization conditions can be used. In a specific embodiment, stringent hybridization conditions are used to identify a homologous GID gene.

Further selection can be carried out on the basis of the properties of the gene, e.g., if the gene encodes a protein product having the isoelectric, electrophoretic, amino acid composition, or partial amino acid sequence of a GID as disclosed herein. Thus, the presence of the gene may be detected by assays based on the physical, chemical, or immunological properties of its expressed product. For example, cDNA clones, or DNA clones which hybrid-select the proper mRNAs, can be selected which produce a polypeptide that, e.g., has similar or identical electrophoretic migration, isoelectric focusing or non-equilibrium pH gel electrophoresis behavior, proteolytic digestion maps, or antigenic properties as known for a GID.

A GID gene can also be identified by mRNA selection, i.e., by nucleic acid hybridization followed by in vitro translation. In this procedure, nucleotide fragments are used to isolate complementary mRNAs by hybridization. Such DNA fragments may represent available, purified GID DNA, or may be synthetic oligonucleotides designed from the partial amino acid sequence information. Immunoprecipitation analysis or functional assays (e.g., GNK and sGNK binding activity or decarboxylase activity) of the in vitro translation products of the products of the isolated mRNAs identifies the mRNA and, therefore, the complementary DNA fragments, that contain the desired sequences. In addition, specific mRNAs may be selected by adsorption of polysomes isolated from cells to immobilized antibodies specifically directed against GID.

The nucleotide sequence of the human GID, SEQ ID NO:1 can also be used to search for highly homologous genes from other species, or for polypeptides having at least one homologous domain, using computer data bases containing either partial or full length nucleic acid sequences as described in the Example below.

Human ESTs can be searched isozymes, for example. The human GID sequence also can be compared with nonhuman sequences, e.g., in GenBank, using GCG software and the blast search program for example. Matches with highly homologous sequences or portions thereof can then be obtained. If the sequence identified is an EST, the insert containing the EST can be obtained and then fully sequenced. The resulting sequence can then be used in place of, and/or in conjunction with SEQ ID NO:1 to identify other ESTs which contain coding regions of the GID homologue (or GID carboxylase domain homologue). Plasmids containing the matched EST for example can be digested with restriction enzymes in order to release the cDNA inserts. If the plasmid does not contain the full length homologue the digests can be purified, e.g., run on an agarose gel and the bands corresponding to the inserts can be cut from the gel and purified. Such purified inserts are likely to contain overlapping regions which can be combined as templates of a PCR assay using primers which are preferably located outside of the GID open reading frame. Amplification should yield the expected product which can be ligated into a vector and used to transform an *E coli* derivative e.g., via TA cloning (Invitrogen) for example. A resulting full-length GID homologue can be placed into an expression vector and the expressed recombinant GID can then be assayed for GNK and sGNK binding activity.

Alternatively, plasmids containing matched EST homologue fragments can be used to transform competent bacteria (e.g., from Gibco BRL, Gaithersburg Md.). Bacteria can be streaked, then grown up overnight. Plasmid preps can be performed (e.g., Quiagen Corp, Santa Clarita Calif.) and the plasmids can be digested by simultaneous restriction digest. Products of the digest can be separated by size on an agarose gel, for example, and purified. The corresponding bands cut from these gels can be ligated to form a full length GID cDNA and used to transform competent bacteria and the resulting plasmid can be purified.

A radiolabeled GID cDNA can be synthesized using the selected mRNA (from the adsorbed polysomes) as a template. The radiolabeled mRNA or cDNA may then be used as a probe to identify homologous GID DNA fragments from among other genomic DNA fragments.

The present invention also relates to cloning vectors containing genes encoding the domains of the GID polypeptides of the invention. The production and use of such derivatives and analogs are within the scope of the present invention.

A modified GID can be made by altering nucleic acid sequences encoding the GID by making substitutions, additions or deletions that provide for functionally equivalent molecules. Preferably, such derivatives are made that have enhanced or increased amino acid decarboxylation activity relative to the native GID. Alternatively, a preferred GID may bind GNK and sGNK more tightly than the native form.

Due to the degeneracy of nucleotide coding sequences, other DNA sequences which encode substantially the same amino acid sequence as a GID gene may be used in the practice of the present invention including those comprising conservative substitutions thereof. These include but are not limited to modified allelic genes, modified homologous genes from other species, and nucleotide sequences comprising all or portions of GID genes which are altered by the substitution of different codons that encode the same amino acid residue within the sequence, thus producing a silent change. Likewise, the GID derivative of the invention can include, but is not limited to, those containing, as a primary amino acid sequence, all or part of the amino acid sequence of a GID polypeptide including altered sequences in which functionally equivalent amino acid residues are substituted for residues within the sequence resulting in a conservative amino acid substitution. And thus, such substitutions are defined as a conservative substitution.

For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to significantly affect apparent molecular weight as determined by polyacrylamide gel electrophoresis, or isoelectric point.

Particularly preferred conservative substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

Amino acid substitutions may also be introduced to substitute an amino acid with a particularly preferable property. For example, a Cys may be introduced at a potential site for disulfide bridges with another Cys. Pro may be introduced because of its particularly planar structure, which induces β-turns in the polypeptide's structure.

The genes encoding GID derivatives and analogs of the invention can be produced by various methods known in the art. The manipulations which result in their production can occur at the gene or polypeptide level. For example, a GID gene sequence can be produced from a native GID clone by any of numerous strategies known in the art [Sambrook et al., 1989, supra]. The sequence can be cleaved at appropriate sites with restriction endonuclease(s), followed by further enzymatic modification if desired, isolated, and ligated in vitro. In the production of the gene encoding a derivative or analog of a GID, care should be taken to ensure that the modified gene remains within the same translational reading frame as the GID gene, uninterrupted by translational stop signals, in the gene region where the desired activity is encoded.

Additionally, the GID-encoding nucleic acid sequence can be produced by in vitro or in vivo mutations, to create and/or destroy translation, initiation, and/or termination sequences, or to create variations in coding regions and/or form new restriction endonuclease sites or destroy pre-existing ones, to facilitate further in vitro modification. Preferably such mutations will further enhance the specific properties of the GID gene product. Any technique for mutagenesis known in the art can be used, including but not limited to, in vitro site-directed mutagenesis [Hutchinson, et al., *J. Biol. Chem.*, 253:6551 (1978); Zoller and Smith, *DNA*, 3:479–488 (1984); Oliphant et al., *Gene*, 44:177 (1986); Hutchinson et al., *Proc. Natl. Acad. Sci. U.S.A.*, 83:710 (1986)], use of TAB® linkers (Pharmacia), etc. PCR techniques are preferred for site-directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61–70). A general method for site-specific incorporation of unnatural amino acids into polypeptides is described in Noren et al., [*Science*, 244:182–188 (1989)]. This method may be used to create analogs with unnatural amino acids.

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Examples of vectors include, but are not limited to, *E. coli*, bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transformation, transfection, infection, electroporation, etc., so that many copies of the gene sequence are generated.

Preferably, the cloned gene is contained on a shuttle vector plasmid, which provides for expansion in a cloning cell, e.g., *E. coli*, and facile purification for subsequent insertion into an appropriate expression cell line, if such is desired. For example, a shuttle vector, which is a vector that can replicate in more than one type of organism, can be prepared for replication in both *E. coli* and *Saccharomyces cerevisiae* by linking sequences from an *E. coli* plasmid with sequences from the yeast 2μ plasmid.

In an alternative method, the desired gene may be identified and isolated after insertion into a suitable cloning vector in a "shot gun" approach. Enrichment for the desired gene, for example, by size fractionation, can be done before insertion into the cloning vector.

Expression of GID Polypeptides

The nucleotide sequence coding for a GID, or a functionally equivalent derivative including a chimeric protein thereof, can be inserted into an appropriate expression vector, i.e., a vector which contains the necessary elements for the transcription and translation of the inserted protein-coding sequence. Such elements are termed herein a "promoter." Thus, the nucleic acid encoding a GID of the invention is operationally associated with a promoter in an expression vector of the invention. Both cDNA and genomic sequences can be cloned and expressed under control of such regulatory sequences. An expression vector also preferably includes a replication origin.

The necessary transcriptional and translational signals can be provided on a recombinant expression vector, or they may be supplied by the native gene encoding the corresponding GID and/or its flanking regions. Any person with skill in the art of molecular biology or protein chemistry, in view of the present disclosure, would readily know how to assay the polypeptide expressed as described herein, to determine whether such a modified polypeptide is indeed a GID. Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

A recombinant GID of the invention, or functionally equivalent derivative, or chimeric construct may be expressed chromosomally, after integration of the coding sequence by recombination. In this regard, any of a number of amplification systems may be used to achieve high levels of stable gene expression [See Sambrook et al., 1989, supra]. Chromosomal integration, e.g., by homologous recombination is desirable where permanent expression is required, such as to immortalize an antibody-producing plasma cell. In other embodiments, such as for in vitro propagation of cells for transplantation, transient transfection such as with a plasmid, is preferable. This way, the cell can be propagated indefinitely in vitro, but will terminally differentiate when reintroduced in vivo.

The cell containing the recombinant vector comprising the nucleic acid encoding a GID is cultured in an appropriate cell culture medium under conditions that provide for expression of the GID by the cell.

Any of the methods previously described for the insertion of DNA fragments into a cloning vector may be used to construct expression vectors containing a gene consisting of appropriate transcriptional/translational control signals and the polypeptide coding sequences. These methods may include in vitro recombinant DNA and synthetic techniques and in vivo recombination (genetic recombination).

Expression of a GID may be controlled by any promoter/enhancer element known in the art, but these regulatory elements must be functional in the host selected for expression. Promoters which may be used to control GID gene expression include, but are not limited to, the SV40 early promoter region [Benoist and Chambon, *Nature*, 290:304–310 (1981)], the promoter contained in the 3 prime long terminal repeat of Rous sarcoma virus [Yamamoto, et al., *Cell*, 22:787–797 (1980)], the herpes thymidine kinase promoter [Wagner et al., *Proc. Natl. Acad. Sci. U.S.A.*, 78:1441–1445 (1981)], the regulatory sequences of the metallothionein gene [Brinster et al., *Nature*, 296:39–42 (1982)]; prokaryotic expression vectors such as the β-lactamase promoter [Villa-Kamaroff, et al., *Proc. Natl. Acad. Sci. U.S.A.*, 75:3727–3731 (1978)], or the tac promoter [DeBoer, et al., *Proc. Natl. Acad. Sci. U.S.A.*, 80:21–25 (1983)]; see also "Useful proteins from recombinant bacteria" in *Scientific American*, 242:74–94 (1980); promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells [Swift et al., *Cell*, 38:639–646 (1984); Ornitz et al., *Cold Spring Harbor Symp. Quant. Biol.*, 50:399–409 (1986); MacDonald, *Hepatology*, 7:425–515 (1987)]; insulin gene control region which is active in pancreatic beta cells [Hanahan, *Nature*, 315:115–122 (1985)], immunoglobulin gene control region which is active in lymphoid cells [Grosschedl et al., Cell, 38:647–658 (1984); Adames et al., Nature, 318:533–538 (1985); Alexander et al., Mol. Cell. Biol., 7:1436–1444 (1987)], mouse mammary tumor virus control region which is active in testicular, breast, lymphoid and mast cells [Leder et al., Cell, 45:485–495 (1986)], albumin gene control region which is active in liver [Pinkert et al., Genes and Devel, 1:268–276 (1987)], alpha-fetoprotein gene control region which is active in liver [Krumlauf et al., Mol. Cell. Biol., 5:1639–1648 (1985); Hammer et al., Science, 235:53–58 (1987)], alpha 1-antitrypsin gene control region which is active in the liver [Kelsey et al., Genes and Devel., 1:161–171 (1987)], beta-globin gene control region which is active in myeloid cells [Mogram et al., Nature, 315:338–340 (1985); Kollias et al., Cell, 46:89–94 (1986)], myelin basic protein gene control region which is active in oligodendrocyte cells in the brain [Readhead et al., Cell, 48:703–712 (1987)], myosin light chain-2 gene control region which is active in skeletal muscle [Sani, Nature, 314:283–286 (1985)], and gonadotropic releasing hormone gene control region which is active in the hypothalamus [Mason et al., Science, 234:1372–1378 (1986)].

Expression vectors containing a nucleic acid encoding a GID of the invention can be identified by many means including by four general approaches: (a) PCR amplification of the desired plasmid DNA or specific mRNA, (b) nucleic acid hybridization, (c) presence or absence of selection marker gene functions, and (d) expression of inserted sequences. In the first approach, the nucleic acids can be amplified by PCR to provide for detection of the amplified product. In the second approach, the presence of a foreign gene inserted in an expression vector can be detected by nucleic acid hybridization using probes comprising sequences that are homologous to an inserted marker gene. In the third approach, the recombinant vector/host system can be identified and selected based upon the presence or absence of certain "selection marker" gene functions (e.g., β-galactosidase activity, thymidine kinase activity, resistance to antibiotics, transformation phenotype, occlusion body formation in baculovirus, etc.) caused by the insertion of foreign genes in the vector. In another example, if the nucleic acid encoding a GID is inserted within the "selection marker" gene sequence of the vector, recombinants containing the GID insert can be identified by the absence of the selection marker gene function. In the fourth approach, recombinant expression vectors can be identified by assaying for the activity, biochemical, or immunological characteristics of the gene product expressed by the recombinant, provided that the expressed polypeptide assumes a functionally active conformation, i.e., the ability of GID to bind GNK and sGNK, and/or decarboxylate amino acids.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., E. coli plasmids col E1, pCR1, pBR322, pMa1-C2, pET, pGEX [Smith et al., Gene, 67:31–40 (1988)], pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

For example, in a baculovirus expression system, both non-fusion transfer vectors, such as but not limited to pVL941 (BamH1 cloning site; Summers), pVL1393 (BamH1, SmaI, XbaI, EcoR1, NotI, XmaIII, BglII, and PstI cloning site; Invitrogen), pVL1392 (BglII, PstI, NotI, XmaIII, EcoRI, XbaI, SmaI, and BamH1 cloning site; Summers and Invitrogen), and pBlueBacIII (BamH1, BglII, PstI, NcoI, and HindIII cloning site, with blue/white recombinant screening possible; Invitrogen), and fusion transfer vectors, such as but not limited to pAc700 (BamH1 and KpnI cloning site, in which the BamH1 recognition site begins with the initiation codon; Summers), pAc701 and pAc702 (same as pAc700, with different reading frames), pAc360 (BamH1 cloning site 36 base pairs downstream of a polyhedrin initiation codon; Invitrogen(195)), and pBlueBacHisA, B, C (three different reading frames, with BamH1, BglII, PstI, NcoI, and HindIII cloning site, an N-terminal peptide for ProBond purification, and blue/white recombinant screening of plaques; Invitrogen (220)) can be used.

Mammalian expression vectors contemplated for use in the invention include vectors with inducible promoters, such as the dihydrofolate reductase (DHFR) promoter, e.g., any expression vector with a DHFR expression vector, or a DHFR/methotrexate co-amplification vector, such as pED (PstI, SalI, SbaI, SmaI, and EcoRI cloning site, with the vector expressing both the cloned gene and DHFR; see Kaufman, Current Protocols in Molecular Biology, 16.12 (1991). Alternatively, a glutamine synthetase/methionine sulfoximine co-amplification vector, such as pEE14 (HindIII, XbaI, SmaI, SbaI, EcoRI, and BclI cloning site, in which the vector expresses glutamine synthase and the cloned gene; Celltech). In another embodiment, a vector that directs episomal expression under control of Epstein Barr Virus (EBV) can be used, such as pREP4 (BamH1, SfiI, XhoI, NotI, NheI, HindIII, NheI, PvuII, and KpnI cloning site, constitutive RSV-LTR promoter, hygromycin selectable marker; Invitrogen), pCEP4 (BamH1, SfiI, XhoI, NotI, NheI, HindIII, NheI, PvuII, and KpnI cloning site, constitutive hCMV immediate early gene, hygromycin selectable marker; Invitrogen), pMEP4 (KpnI, PvuI, NheI, HindIII, NotI, XhoI, SfiI, BamH1 cloning site, inducible methallothionein IIa gene promoter, hygromycin selectable marker: Invitrogen), pREP8 (BamH1, XhoI, NotI, HindIII, NheI, and KpnI cloning site, RSV-LTR promoter, histidinol selectable marker; Invitrogen), pREP9 (KpnI, NheI, HindIII, NotI, XhoI, SfiI, and BamHI cloning site, RSV-LTR promoter, G418 selectable marker; Invitrogen), and pEBVHis (RSV-LTR promoter, hygromycin selectable marker, N-terminal peptide purifiable via ProBond resin and cleaved by enterokinase; Invitrogen). Selectable mammalian expression vectors for use in the invention include pRc/CMV (HindIII, BstXI, NotI, SbaI, and ApaI cloning site, G418 selection; Invitrogen), pRc/RSV (HindIII, SpeI, BstXI, NotI, XbaI cloning site, G418 selection; Invitrogen), and others. Vaccinia virus mammalian expression vectors (see, Kaufman, 1991, supra) for use according to the invention include but are not limited to pSC11 (SmaI cloning site, TK- and β-gal selection), pMJ601 (SalI, SmaI, AflI, NarI, BspMII, BamHI, ApaI, NheI, SacII, KpnI, and HindIII cloning site; TK- and β-gal selection), and pTKgptF1S (EcoRI, PstI, SalI, AccI, HindII, SbaI, BamHI, and Hpa cloning site, TK or XPRT selection).

Additional inducible promoters include a tetracycline promoter or an ecdysone promoter for regulating the expression levels of the polypeptide in the cells.

Yeast expression systems can also be used according to the invention to express the GID polypeptide. For example, the non-fusion pYES2 vector (XbaI, SphI, ShoI, NotI, GstXI, EcoRI, BstXI, BamH1, SacI, Kpn1, and HindIII cloning sit; Invitrogen) or the fusion pYESHisA, B, C (XbaI, SphI, ShoI, NotI, BstXI, EcoRI, BamH1, SacI, KpnI, and HindIII cloning site, N-terminal peptide purified with Pro-Bond resin and cleaved with enterokinase; Invitrogen), to mention just two, can be employed according to the invention.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Different host cells have characteristic and specific mechanisms for the translational and post-translational processing and modification (e.g., glycosylation, cleavage [e.g., of signal sequence]) of polypeptides. Appropriate cell lines or host systems can be chosen to ensure the desired modification and processing of the foreign polypeptide expressed. For example, expression in a bacterial system can be used to produce an non-glycosylated core protein product. Expression in yeast can produce a glycosylated product. Expression in eukaryotic cells can increase the likelihood of "native" glycosylation and folding of a heterologous polypeptide. Moreover, expression in mammalian cells can provide a tool for reconstituting, or constituting, the GID activity. Furthermore, different vector/host expression systems may affect processing reactions, such as proteolytic cleavages, to a different extent.

Vectors are introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter [see, e.g., Wu et al., *J. Biol. Chem.* 267:963–967 (1992); Wu and Wu, *J. Biol. Chem.*, 263:14621–14624 (1988); and Hartmut et al., Canadian Patent Application No. 2,012,311, filed Mar. 15, 1990].

General Polypeptide Purification Procedures

One preferred method of purifying GID is described in the Example below. In general, however, initial steps for purifying a GID of the present invention can include salting in or salting out, such as in ammonium sulfate fractionations; solvent exclusion fractionations, e.g., an ethanol precipitation; detergent extractions to free membrane bound polypeptides using such detergents as TRITON X-100, TWEEN-20 etc.; or high salt extractions. Solubilization of polypeptides may also be achieved using aprotic solvents such as dimethyl sulfoxide and hexamethylphosphoramide. In addition, high speed ultracentrifugation may be used either alone or in conjunction with other extraction techniques.

Generally good secondary isolation or purification steps include solid phase absorption using calcium phosphate gel or hydroxyapatite; or solid phase binding. Solid phase binding may be performed through ionic bonding, with either an anion exchanger, such as diethylaminoethyl (DEAE), or diethyl [2-hydroxypropyl]aminoethyl (QAE) SEPHADEX or cellulose; or with a cation exchanger such as carboxymethyl (CM) or sulfopropyl (SP) SEPHADEX or cellulose. Alternative means of solid phase binding includes the exploitation of hydrophobic interactions e.g., the using of a solid support such as phenylSepharose and a high salt buffer; affinity-binding, using, e.g., placing GNK and sGNK on an activated support; immuno-binding, using e.g., an antibody to a GID bound to an activated support; as well as other solid phase supports including those that contain specific dyes or lectins etc. A further solid phase support technique that is often used at the end of the purification procedure relies on size exclusion, such as SEPHADEX and SEPHAROSE gels, or pressurized or centrifugal membrane techniques, using size exclusion membrane filters.

Solid phase support separations are generally performed batch-wise with low-speed centrifugations or by column chromatography. High performance liquid chromatography (HPLC), including such related techniques as FPLC, is presently the most common means of performing liquid chromatography. Size exclusion techniques may also be accomplished with the aid of low speed centrifugation.

In addition size permeation techniques such as gel electrophoretic techniques may be employed. These techniques are generally performed in tubes, slabs or by capillary electrophoresis.

Almost all steps involving polypeptide purification employ a buffered solution. Unless otherwise specified, generally 25–100 mM concentrations of buffer salts are used. Low concentration buffers generally imply 5–25 mM concentrations. High concentration buffers generally imply concentrations of the buffering agent of between 0.1–2M concentrations. Typical buffers can be purchased from most biochemical catalogues and include the classical buffers such as Tris, pyrophosphate, monophosphate and diphosphate and the Good buffers [Good, N. E., et al., *Biochemistry*, 5:467 (1966); Good, N. E. and Izawa, S., *Meth. Enzymol.*, 24B:53 (1972); and Fergunson, W. J. and Good, N. E., *Anal. Biochem.*, 104:300 (1980] such as Mes, Hepes, Mops, tricine and Ches.

Materials to perform all of these techniques are available from a variety of sources such as Sigma Chemical Company in St. Louis, Mo.

Antibodies to the GID Polypeptides of the Present Invention

According to the present invention, the GID polypeptide as produced by a recombinant source, or through chemical synthesis, or a GID polypeptide isolated from natural sources; and derivatives or analogs thereof, including fusion proteins, may be used as an immunogen to generate antibodies that recognize the GID polypeptide, as exemplified below. Such antibodies include but are not limited to polyclonal, monoclonal, chimeric including humanized chimeric, single chain, Fab fragments, and a Fab expression library. The anti-GID antibodies of the invention may be cross reactive, that is, they may recognize a GID polypeptide derived from a different source. Polyclonal antibodies have greater likelihood of cross reactivity. Alternatively, an antibody of the invention may be specific for a single form of a GID polypeptide, such as a particular fragment of the hGID having the amino acid sequence of SEQ ID NO:2.

Thus the present invention provides compositions and uses of antibodies that are immunoreactive with GID polypeptides. Such antibodies "bind specifically" to GID polypeptides, meaning that they bind via antigen-binding sites of the antibody as compared to non-specific binding interactions. The terms "antibody" and "antibodies" are used herein in their broadest sense, and include, without limitation, intact monoclonal and polyclonal antibodies as well as fragments such as Fv, Fab, and F(ab')2 fragments, single-chain antibodies such as scFv, and various chain combinations. In some embodiments, the antibodies of the present invention are humanized antibodies or human antibodies. The antibodies may be prepared using a variety of well-known methods including, without limitation, immunization of animals having native or transgenic immune repertoires, phage display, hybridoma and recombinant cell culture, and transgenic plant and animal bioreactors.

Both polyclonal and monoclonal antibodies may be prepared by conventional techniques. See, for example, *Monoclonal Antibodies, Hybridomas: A New Dimension in Biological Analyses*, Kennet et al. (eds.), Plenum Press, New York (1980); and *Antibodies: A Laboratory Manual*, Harlow and Land (eds.), Cold Spring Harbor Laboratory Press, Cold Spring Harbor, N.Y., (1988).

Various procedures known in the art may be used for the production of polyclonal antibodies to GID or derivative or analog thereof. For the production of antibody, various host animals can be immunized by injection with the GID, or a derivative (e.g., or fusion protein) thereof, including but not limited to rabbits, mice, rats, sheep, goats, etc. In one embodiment, the GID can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward the GID polypeptide, or analog, or derivative thereof, any technique that provides for the production of antibody molecules by continuous cell lines in culture may be used. These include but are not limited to the hybridoma technique originally developed by Kohler and Milstein [*Nature*, 256:495–497 (1975)], as well as the trioma technique, the human B-cell hybridoma technique [Kozbor et al., *Immunology Today*, 4:72 (1983); Cote et al., *Proc. Natl. Acad. Sci. U.S.A.*, 80:2026–2030 (1983)], and the EBV-hybridoma technique to produce human monoclonal antibodies [Cole et al., in *Monoclonal Antibodies and Cancer Therapy*, Alan R. Liss, Inc., pp. 77–96 (1985)]. In an additional embodiment of the invention, monoclonal antibodies can be produced in germ-free animals utilizing recent technology [PCT/US90/02545].

The monoclonal antibodies of the present invention include chimeric antibodies, e.g., "humanized" versions of antibodies originally produced in mice or other non-human species. Such humanized antibodies may be prepared by known techniques and offer the advantage of reduced immunogenicity when the antibodies are administered to humans. In fact, according to the invention, techniques developed for the production of "chimeric antibodies" [Morrison et al., *J. Bacteriol.*, 159:870 (1984); Neuberger et al., *Nature*, 312:604–608 (1984); Takeda et al., *Nature*, 314:452–454 (1985)] by splicing the genes from a mouse antibody molecule specific for a GID together with genes from a human antibody molecule of appropriate biological activity can be used; such antibodies are within the scope of this invention.

Thus, a humanized antibody is an engineered antibody that typically comprises the variable region of a non-human (e.g., murine) antibody, or at least complementarity determining regions (CDRs) thereof, and the remaining immunoglobulin portions derived from a human antibody. Procedures for the production of chimeric and further engineered monoclonal antibodies include those described Riechmann et al., [*Nature* 332:323, (1988)]; Liu et al.,[*Proc. Nat. Acad. Sci.* 84:3439 (1987)]; Larrick et al., [*Bio/Technology* 7:934, (1989)]; and Winter and Harris, [*TIBS* 14:139, (May, 1993)]. Such human or humanized chimeric antibodies are preferred for use in therapy of human diseases or disorders (described infra), since the human or humanized antibodies are much less likely than xenogenic antibodies to induce an immune response, in particular an allergic response, themselves.

Therefore, procedures that have been developed for generating human antibodies in non-human animals may be employed in producing antibodies of the present invention. The antibodies may be partially human or preferably completely human. For example, transgenic mice into which genetic material encoding one or more human immunoglobulin chains has been introduced may be employed. Such mice may be genetically altered in a variety of ways. The genetic manipulation may result in human immunoglobulin polypeptide chains replacing endogenous immunoglobulin chains in at least some, and preferably virtually all, antibodies produced by the animal upon immunization. Mice in which one or more endogenous immunoglobulin genes have been inactivated by various means have been prepared. Human immunoglobulin genes have been introduced into the mice to replace the inactivated mouse genes. Antibodies produced in the animals incorporate human immunoglobulin polypeptide chains encoded by the human genetic material introduced into the animal. Examples of techniques for the production and use of such transgenic animals to make antibodies (which are sometimes called "transgenic antibodies") are described in U.S. Pat. Nos. 5,814,318, 5,569,825, and 5,545,806, which are incorporated by reference herein.

Hybridoma cell lines that produce monoclonal antibodies specific for the polypeptides of the invention are also provided by the present invention. Such hybridomas may be produced and identified by conventional techniques. One method for producing such a hybridoma cell line comprises immunizing an animal with a polypeptide, harvesting spleen cells from the immunized animal, fusing said spleen cells to a myeloma cell line, thereby generating hybridoma cells, and identifying a hybridoma cell line that produces a monoclonal antibody that binds the polypeptide. The monoclonal antibodies produced by hybridomas may be recovered by conventional techniques.

According to the invention, techniques described for the production of single chain antibodies [U.S. Pat. Nos. 5,476, 786 and 5,132,405 to Huston; U.S. Pat. No. 4,946,778] can be adapted to produce e.g., GID-specific single chain antibodies. An additional embodiment of the invention utilizes the techniques described for the construction of Fab expression libraries [Huse et al., *Science*, 246:1275–1281 (1989)] to allow rapid and easy identification of monoclonal Fab fragments with the desired specificity for a GID, or its derivatives, or analogs.

Antibody fragments which contain the idiotype of the antibody molecule can be generated by known techniques. For example, such fragments include but are not limited to:

the F(ab')₂ fragment which can be produced by pepsin digestion of the antibody molecule; the Fab' fragments which can be generated by reducing the disulfide bridges of the F(ab')₂ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), Western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of GID, one may assay generated hybridomas for a product which binds to the GID fragment containing such epitope and choose those which do not cross-react with GID. For selection of an antibody specific to a GID from a particular source, one can select on the basis of positive binding with GID expressed by or isolated from that specific source.

The foregoing antibodies can be used in methods known in the art relating to the localization and activity of the GID, e.g., for Western blotting, imaging GID in situ, measuring levels thereof in appropriate physiological samples, etc. using any of the detection techniques mentioned herein or known in the art.

In a specific embodiment, antibodies that agonize or antagonize the activity of GID can be generated. Such antibodies can be tested using the assays described infra for identifying ligands.

Labels

The GID polypeptides of the present invention, antibodies to the GID polypeptides, nucleic acids that hybridize to SEQ ID NO:1 (e.g. probes) etc. can all be labeled. Suitable labels include enzymes, fluorophores (e.g., fluorescein isothiocyanate (FITC), phycoerythrin (PE), Texas red (TR), rhodamine, free or chelated lanthanide series salts, especially $Eu^{3+}$, to name a few fluorophores), chromophores, radioisotopes, chelating agents, dyes, colloidal gold, latex particles, ligands (e.g., biotin), and chemiluminescent agents. When a control marker is employed, the same or different labels may be used for the receptor and control marker.

In the instance where a radioactive label, such as the isotopes $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

Direct labels are one example of labels which can be used according to the present invention. A direct label has been defined as an entity, which in its natural state, is readily visible, either to the naked eye, or with the aid of an optical filter and/or applied stimulation, e.g. ultraviolet light to promote fluorescence. Among examples of colored labels, which can be used according to the present invention, include metallic sol particles, for example, gold sol particles such as those described by Leuvering (U.S. Pat. No. 4,313,734); dye sole particles such as described by Gribnau et al. (U.S. Pat. No. 4,373,932) and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionucleotide, a fluorescent moiety or a luminescent moiety. In addition to these direct labeling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in *Methods in Enzymology,* 70:419–439 (1980) and in U.S. Pat. No. 4,857,453. Suitable enzymes include, but are not limited to, alkaline phosphatase and horseradish peroxidase.

In addition, a GID or fragment thereof can be modified to contain a marker protein such as green fluorescent protein as described in U.S. Pat. No. 5,625,048 filed Apr. 29, 1997, WO 97/26333, published Jul. 24, 1997 and WO 99/64592 the contents of all of which are hereby incorporated by reference in their entireties.

Other labels for use in the invention include magnetic beads or magnetic resonance imaging labels.

In another embodiment, a phosphorylation site can be created on an antibody of the invention for labeling with $^{32}P$, e.g., as described in European Patent No. 0372707 (application No. 89311108.8) by Sidney Pestka, or U.S. Pat. No. 5,459,240, issued Oct. 17, 1995 to Foxwell et al.

As exemplified herein, polypeptides, including antibodies, can be labeled by metabolic labeling. Metabolic labeling occurs during in vitro incubation of the cells that express the polypeptide in the presence of culture medium supplemented with a metabolic label, such as [$^{35}S$]-methionine or [$^{32}P$]-orthophosphate. In addition to metabolic (or biosynthetic) labeling with [$^{35}S$]-methionine, the invention further contemplates labeling with [$^{14}C$]-amino acids and [$^3H$]-amino acids (with the tritium substituted at non-labile positions).

Drug Screens

In addition to rational design of agonists and antagonists based on the structure of GID the present invention further contemplates an alternative method for identifying specific antagonists or agonists using various screening assays known in the art.

Accordingly any screening technique known in the art can be used to screen for agonists or antagonists to GID. The present invention contemplates screens for small molecule ligands or ligand analogs and mimics, as well as screens for natural ligands that bind to and agonize or antagonize GID in vivo. For example, natural products libraries can be screened using assays of the invention for molecules that agonize or antagonize GID activity.

In a particular embodiment, the drug screen is performed with a mammalian cell that comprises a GID.

Knowledge of the primary sequence of GID polypeptide and the similarity of several domains with those contained in other polypeptides, can also provide clues for identifying inhibitors or antagonists of the polypeptide. Identification and screening of antagonists is further facilitated by determining structural features of the polypeptide, e.g., using X-ray crystallography, neutron diffraction, nuclear magnetic resonance spectrometry, and other techniques for structure determination. These techniques provide for the rational design or identification of agonists and antagonists.

Another approach uses recombinant bacteriophage to produce large libraries. Using the "phage method" [Scott and Smith, Science 249:386–390 (1990); Cwirla, et al., Proc. Natl. Acad. Sci., 87:6378–6382 (1990); Devlin et al., Science, 249:404–406 (1990)], very large libraries can be constructed ($10^6$–$10_8$ chemical entities). A second approach uses primarily chemical methods, of which the Geysen method [Geysen et al., Molecular Immunology 23:709–715 (1986); Geysen et al. J. Immunologic Method 102:259–274 (1987)] and the method of Fodor et a. [Science 251:767–773 (1991)] are examples. Furka et al. [14th International Congress of Biochemistry, Volume 5, Abstract FR:013 (1988); Furka, Int. J. Peptide Protein Res. 37:487–493 (1991)], Houghton [U.S. Pat. No. 4,631,211, issued December 1986] and Rutter et al. [U.S. Pat. No. 5,010,175, issued Apr. 23, 1991] describe methods to produce a mixture of peptides that can be tested as agonists or antagonists.

In another aspect, synthetic libraries [Needels et al., Proc. Natl. Acad. Sci. USA 90:10700–10704 (1993); Ohlmeyer et al., Proc. Natl. Acad. Sci. USA 90:10922–10926 (1993); Lam et al., International Patent Publication No. WO 92/00252; Kocis et al., International Patent Publication No. WO 9428028, each of which is incorporated herein by reference in their entireties], and the like can be used to screen for binding partners/ligands to the GID polypeptide according to the present invention. In addition, a library of chemicals as are commercially available from most large chemical companies including Merck, Glaxo Welcome, Bristol Meyers Squib, Monsanto/Searle, Eli Lilly, Aventis and Pharmacia UpJohn, can be screened including via high throughput screening. Alternatively potential drugs may be synthesized de novo.

Assays for GID-binding partners in cells that express the GID polypeptide (or extracts thereof) can be performed. The binding partners can be provided readily as recombinant or synthetic polypeptides for example. Alternatively, small organic molecules or phage peptides can be used in the assays.

The screening can be performed with recombinant cells (or extracts thereof) that express a GID polypeptide, or fragment thereof, e.g. the portion of GID polypeptide required for binding GNK and sGNK. Alternatively, the screening can be performed using purified polypeptide, e.g., produced recombinantly, as described above. The ability of the labeled, soluble or solubilized GID polypeptide to bind GNK and sGNK can be determined. In either case, such assays can be used to screen libraries, as described in the foregoing references and below.

In one such example, a phage library can be employed as the source of potential modulators. Phage libraries have been constructed which when infected into host E. coli produce random peptide sequences of approximately 10 to 15 amino acids [Parmley and Smith, Gene, 73:305–318 (1988), Scott and Smith, Science, 249:386–249 (1990)]. Specifically, the phage library can be mixed in low dilutions with permissive E. coli in low melting point LB agar which is then poured on top of LB agar plates. After incubating the plates at 37° C. for a period of time, small clear plaques in a lawn of E. coli will form which represents active phage growth and lysis of the E. coli. A representative of these phages can be absorbed to nylon filters by placing dry filters onto the agar plates. The filters can be marked for orientation, removed, and placed in washing solutions to block any remaining absorbent sites. The filters can then be placed in a solution containing, for example, a radioactive fragment of GID polypeptide containing the GNK and/or sGNK binding domains. After a specified incubation period, the filters can be thoroughly washed and developed for autoradiography. Plaques containing the phage that bind to the radioactive GNK and/or sGNK binding domains of GID polypeptide can then be identified. These phages can be further cloned and then retested for their ability to hinder the binding of GID polypeptide to GNK and/or sGNK, for example. Once the phages have been purified, the binding sequence contained within the phage can be determined by standard DNA sequencing techniques. Once the DNA sequence is known, synthetic peptides can be generated which represents these sequences. These peptides can be re-tested, for example, for their ability to interfere with GID polypeptide binding to GNK and sGNK, for example.

The effective peptide(s) can be synthesized in large quantities for use in vivo models. It should be emphasized that synthetic peptide production is relatively non-labor intensive, easily manufactured, quality controlled and thus, large quantities of the desired product can be produced quite cheaply. Similar combinations of mass produced synthetic peptides have recently been used with great success [Patarroyo, Vaccine, 10:175–178 (1990)].

Similarly, antagonists and agonists to the decarboxylation activity of GID can be obtained. In this case the enzymatic activity can be assayed, e.g., using an amino acid substrate comprising a $^{14}C$-labeled carboxyl group and measuring the liberation of the isotope as $^{14}CO_2$ [Okuno and Fujisawa, Anal. Biochem. 129:405–411 (1983)].

In addition, the present invention provides assays for caspase-3 using the purified GID of the present invention as a substrate as described in the Example below. For example, caspase-3 activation can be determined by monitoring/assaying the cleavage of GID in lysates using antibodies that are specific for the GID cleavage products and/or the full length GID. In a particular embodiment a Western blot is performed as part of the assay.

The present invention may be better understood by reference to the following non-limiting Example, which is provided as exemplary of the invention. The following example is presented in order to more fully illustrate the preferred embodiments of the invention. It should in no way be construed, however, as limiting the broad scope of the invention.

EXAMPLE

GID is a Member of the Amino Acid Decarboxylase Family and a Substrate for Caspase-3

Methods and Results

Purification of GID

Lungs were isolated from seventy New Zealand white rabbits intravenously injected with 100 µg/kg of human recombinant IL-1α, fifteen minutes prior to sacrifice. Following sacrifice, lungs were rapidly removed, washed in conventional ice cold phosphate buffered saline (cold PBS), immediately fast frozen, and stored at −80° C. The lungs were homogenized using a Brinkman tissue homogenizer. Tissue and cellular debris was removed by centrifugation and ultrafiltration. The resulting supernatant was made 25% with respect to ammonium sulphate and proteins precipitated by this 0–25% salt cut were collected by centrifugation. Pelleted proteins were resuspended and sequentially subjected to the following purification steps:
 (1) ion-exchange chromatography using Source 15 Q (Pharmacia);
 (2) dye affinity chromatography using Reactive Green 19 (Sigma Chemicals);
 (3) size exclusion chromatography using Superdex 200 (Pharmacia);
 (4) affinity chromatography using heparin-sepharose (Pharmacia);
 (5) ion-exchange chromatography using Mono Q resin (Pharmacia);
 (6) size exclusion chromatography using SEC-400 (BioRad);
 (7) ion-exchange chromatography using a microbore Mono Q column; and
 (8) electrophoretic separation using SDS-PAGE with 8–16% polyacrylamide gradient gels (Novex).

The final chromatographic step, fractionation on a microbore MonoQ column containing 35 μl resin, was performed to concentrate the sample in a small volume for electrophoresis. Briefly, fractions containing GNK, sGNK, and GID from the SEC-400 chromatography step, were loaded onto the Mono Q column, previously equilibrated in 20 mM Tris-HCl, pH 8.5, 10 mM β-glycerophosphate, 1 mM dithiothreitol (DTT), 1 mM EDTA, 1 mM EGTA, 1 mM phenylmethyl sulphonyl fluoride (PMSF), 0.1 mM leupeptin, 10% glycerol and 0.1% NP-40 (Buffer A), at a flow rate of 50 μl/min. After loading, the column was washed with 10 column volumes of Buffer A. Bound polypeptides, which included GNK, sGNK, and GID, were eluted using a 500 μl linear 0–500 mM NaCl gradient in Buffer A.

The fraction containing GNK, sGNK, and GID was subjected to SDS-PAGE on an 8–16% Tris-glycine gradient gel (Novex). Bands were visualized by silver staining. GID was identified (referred to as Band 8) and excised from the gel. Trypsin digestion was performed in situ and resulting peptides were extracted by methods known in the art. The isolated peptides were analyzed by mass spectroscopy. The amino acid sequences of several peptides were ascertained and these sequences were utilized to design oligonucleotide probes for use in the molecular cloning of GID.

Cloning and Sequencing of Human GID

The amino acid sequence for GID was obtained by mass spectrometry following the polyacrylamide gel electrophoresis of a rabbit lung preparation, an in-gel protease digestion, and the extraction of the resulting peptides [Rosenfeld et al., *Anal. Biochem.* 203:173–179 (1992); Henzel et al., *Methods of Enzymology* 6:239–247 (1994); Hellman et al., *Anal. Biochem.* 224:451–455 (1995); and Kussmann et al., *J. Mass Spectr.* 32:593–601 (1997)]. Peptides denoted as Band 8.2, 8.4, and 8.9 were sequenced. A human EST having the accession no. T67909 was identified as the human homolog to the lapin Band 8.2 peptide. In addition, another human EST, having the accession no. R82536, was homologous to the Band 8.4 and Band 8.9 peptides.

PCR amplification primers: Primers were designed from the portion of T67909 covered by Band 8.2 peptide.

```
(a) 5'primer: GGC AGA TCC CTG TAG TGG G       (SEQ ID NO:13); and
(b) 3'primer: TAA GTC TTC AAT GTG ACT GAC T   (SEQ ID NO:14)
```

A 271bp double-stranded PCR fragment was generated by PCR amplification of λgt10 HDF library phage using the primers having the nucleotide sequences of SEQ ID NOs:13 and 14. A single-stranded probe was then made by combining two separate PCR reactions of 4 ng and 8 ng of the double-stranded template fragment containing 50 pMol of the primer having the nucleotide sequence of SEQ ID NO:13. This probe was then used to screen 500,000 plaques from a λgt10 HDF library. Three positive clones were identified: HDF8-3-1, HDF8-12-1, and HDF8-18-1. HDF8-3-1 extended the EST in both directions.

Next, EST R82536 was linked to T67909. A 1224bp fragment from λgt10 KB (human epidermal carcinoma cell line) library phage was amplified by PCR using the following primers:
 (c) 5' primer: GAC TTT AGT TGC TGG TCT TAC A (SEQ ID NO:15); and a 3' primer having the nucleotide sequence of SEQ ID NO:14.

This PCR product was sequenced and EST T67909 was linked to EST R82536. A single stranded probe was generated by amplifying 10 ng of the double-stranded KB fragment in a PCR reaction containing 50 pMol of a 3' primer:
 (d) GAG CTG GTC TCA CTC AAA GC (SEQ ID NO:16).

The probe was then used to screen approximately 500,000 plaques from a λgt10 KB library. A number of positives were identified.

Approximately 35 of the positive primary plaques were picked and analyzed by amplification with a combination of primers derived from the sequence and primers from the λgt10 vector. The primers were:
 (e) CAG TTG ACA GGC ATG CTT GAT (SEQ ID NO:17, cDNA primer, directed toward the 5' end of the mRNA)
 (f) CGA GCT GCT CTA TAG ACT GCT GGG TAG TCC (SEQ ID NO:18, vector primer, left arm)
 (g) TAA CAG AGG TGG CTT ATG AGT ATT TCT TCC (SEQ ID NO:19, vector primer, right arm)

KB8-1-7 was identified as extending HDF8-3-1 further in the 5' direction.

Next, approximately 50 more positive primary plaques were picked and analyzed by amplification with a combination of primers. The primers were
 (i) GGT GGT ATC TGA AAG TAT CC, (SEQ ID NO:20) designed from KB8-1-7, directed toward the 5' end and vector primers having the nucleotide sequences of SEQ ID NOs:18 and 19. An approximately 900 bp fragment was amplified in KB8-11-1, which would indicate that this clone was a potential candidate to extend HDF8-3-1 in the 5' direction. However, the sequence of KB8-11-1 did not extend Band 8 in the 5' direction. Therefore, the 900 bp PCR fragment cannot be explained since the 3' primer from above, SEQ ID NO:20, does not hybridize to KB8-11-1. KB8-11-1overlapped HDF8-3-1 and was useful as a second source for the 3' end of Band 8.

Thirty clones were also analyzed with internal primers:

5' primer: (h) GGA TAC TTT CAG ATA CCA CC (SEQ ID NO:21); and the 3' primer having the nucleotide sequence of SEQ ID NO:17.

A 742 bp product was observed in 8 clones including KB8-10-5. When KB8-10-5 was then amplified in a manner similar to KB8-11-1 in the previous paragraph, an approximately 600 bp PCR fragment was sequenced and identified as extending KB8-1-7 41 nucleotides in the 5' direction.

A probe was then made to screen a λgt10 NK (human natural killer cell) library. A 552 bp double-stranded PCR fragment was amplified by PCR from the primary phage, KB8-10-5 using the following primers:

5'primer: (j) AGG AGG AAG TAG AGC CCG GG   (SEQ ID NO:22); and

3'primer: (k) ACA TTG AAG CCA TCC ACT ACG AA   (SEQ ID NO:23).

A single-stranded probe was then generated by amplifying 7.5 ng of the double-stranded template fragment containing 50 pMol of the 3' primer having the nucleotide sequence of SEQ ID NO:22. The probe was then used to screen 500,000 plaques from a λgt10 NK library. Eight positive clones were identified.

These 8 primary clones were picked and analyzed by amplification with a combination of primers derived from the sequence and primers from λgt 10 vector. The primers had the nucleotide sequences of SEQ ID NOs:18, 19 and 23. NK8-4-1 was identified as extending Band 8 in the 5' direction. This clone has a 1757 bp unspliced intron.

The regions corresponding to bp1–924 and bp1781–3356 were derived from at least two different sources. Therefore, the intervening bp925–1780 sequence was confirmed by amplifying other RNA sources. KB, Clone22 T-cell line, and NK first strand cDNA were amplified with the 5' primer having the nucleotide sequence of SEQ ID NO:21; and the 3' primer: (l) GTT AGG TCA GAT TCC AGT TC (SEQ ID NO:24). PCR products KB8-PCR, Clone22-8-PCR, and NK8-PCR were directly sequenced. A full-length construct was made with $NH_2$-terminal HIS and COOH-terminal myc tags. Since none of the clones were full-length, overlapping clones KB8-11-1 and KB8-1-7 were PCR amplified and recombined by restriction enzyme digestion to generate a full-length clone.

The clones listed in Table 1 and PCR products form a complete composite of Band 8 having the nucleic acid sequence of SEQ ID NO:1 and the amino acid sequence of SEQ ID NO:2 (see also FIG. 1). A related open reading frame has previously been described as a partial open reading frame of the KIAA0251 gene, in a disclosure of the sequencing of 80 unidentified human genes [Nagase et al., DNA Research 3:321–329 (1996)].

TABLE 1

Clone Dimensions

| | |
|---|---|
| NK8-4-1 | bp1–819 and then bp820–924 (this clone has a 1757bp unspliced intron) |
| KB8-1-7 | bp157–2064 |
| HDF8-3-1 | bp1781–3356 |
| KB8-11-1 | bp1724–3735 |
| KB8-PCR | bp528–1846 |
| Clone 22-8-PCR | Bp528–1836 |
| NK8-PCR | bp540–1848 |

TABLE 2

Primer Dimensions

| PRIMER | SEQ ID NO: | DESCRIPTION |
|---|---|---|
| (a) | 13 | bp2087–2105 |
| (b) | 14 | bp2358–2337 |
| (c) | 15 | bp1134–1155 |
| (d) | 16 | bp2336–2317 |
| (e) | 17 | bp1260–1240 |
| (f) | 18 | vector primer |
| (g) | 19 | vector primer |
| (h) | 20 | bp518–537 |
| (i) | 21 | bp537–518 |
| (j) | 22 | bp122–141 |
| (k) | 23 | bp674–652 |
| (l) | 24 | bp1850–1831 |

GID/Band 8 Tissue Distribution

To determine the distribution of GID in human tissues, PCR analysis was performed using human cDNA templates and oligonucleotide primers designed to be specific for GID. The following oligonucleotide primers were used in the PCR amplifications:

5'oligo (PMH22):
   5'GGCTTGCCCTTGCCCTGCTTGTGCCGTGTA 3'   (SEQ ID NO:25)
3'oligo (PMH23):
   5'CCACAGAGGCAGGGCACGGAGTTTGTCTGTG 3'   (SEQ ID NO:26)

Oligos were designed to amplify a 444 bp region (nt 631–1075) over the decarboxylase domain of GID cDNA. For the PCR amplifications, each 25 μl reaction contained 0.2 ng of a particular cDNA template, 12 pmol each primer, 100 μM each dNTP and 1.25 U Taq DNA polymerase in 1.5 mM MgCl2, 50 mM KCl, 10 mM Tris-HCl pH8.3 and 0.01% gelatin.

Figure 2:
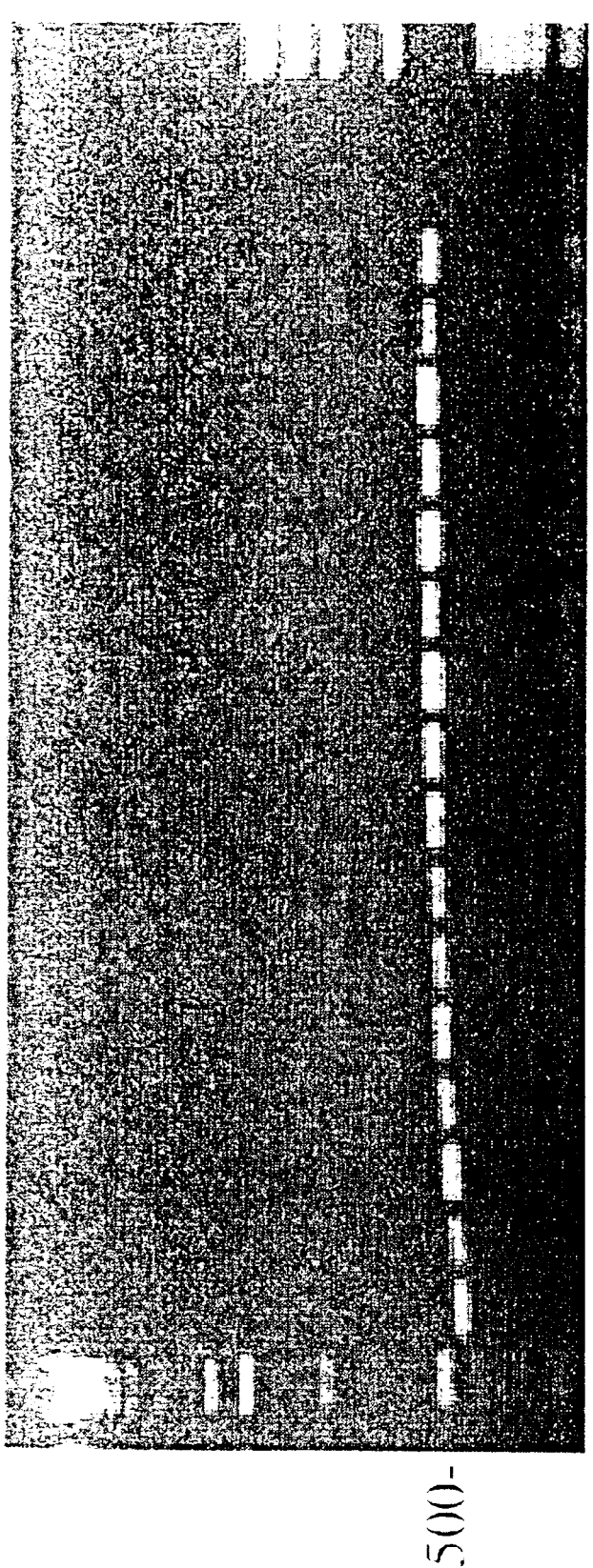
FIG. 2 is a depiction of a 1% agarose gel (following electrophoresis and ethidium bromide staining) used to display the distribution of GID in human tissues. To determine the distribution of GID in human tissues, PCR analysis was performed using human cDNA templates and oligonucleotide primers designed to be specific for GID. The determination was performed as described in the Example below. The samples differed only by the cDNA template that was included in each reaction mixture. Unless otherwise stated, the tissue samples listed are human tissues. Lanes 1–20 contained the following: (1) molecular weight marker, 1 kb ladder; (2) breast carcinoma cDNA, GI-101; (3) lung carcinoma, LX-1; (4) colon adenocarcinoma, CX-1; (5) lung carcinoma, GI-117; (6) prostatic adenocarcinoma, PC-3; (7) colon adenocarcinoma, GI-112; (8) ovarian adenocarcinoma, GI-102; (9) pancreatic adenocarcinoma, GI-103; (10) brain; (11) heart; (12) kidney; (13) liver; (14) lung; (15) pancreas; (16) small intestine; (17) skeletal muscle; (18) no DNA template control; (19) blank lane; and (20) molecular weight marker φX174-HaeIII.

The amplification conditions were 95° C. denaturation for 2 min, followed by 1 min at 95° C., 1 min at 58° C. and 1 min at 72° C. for 35 cycles. The samples were analyzed on a 1% agarose gel. All samples differed only by the cDNA template that was included in each reaction mixture. The results are shown in FIG. 2.

Based on PCR analysis using primers specific for GID to amplify GID sequences from a variety of human tissues, GID expression appears to be ubiquitous. PCR results were positive for all the tissues analyzed.

In a related study, λgt10 library phage were amplified with primers having the nucleotide sequences of SEQ ID NOs:13 and 14. A PCR product was observed in Raji (human B cell line), Clone 22, KB, IIDF, NK, Human placenta, WI26 VA4 (human embryonic lung fibroblast), Hut102, SKHep (human hepatocarcinoma cell line), Human stromal bone marrow, and PBL (human peripheral blood lymphocytes). There was no product in human bone marrrow, HBT (human bladder tumor), HPT-4 (human pancreatic tumor), and PBL (human peripheral blood thymocytes). The same library panel was amplified with primers having the nucleotide sequences of SEQ ID NOs: 4 and 15. Raji, Clone22, KB, HDF, NK, WI26, SkHep, Human stromal bone marrow, and PBL were positive. The remaining lambda libraries were negative. Finally, the same library panel was amplified with primers having the nucleotide sequences of SEQ ID NOs: 22 and 23. Raji, Clone22, KB, HDF, NK, Placenta, SKHep, Human stromal bone marrow, and PBL were positive. The remaining lambda libraries were negative.

GID can Associate with GNK in 293 Cells

Figure 3:
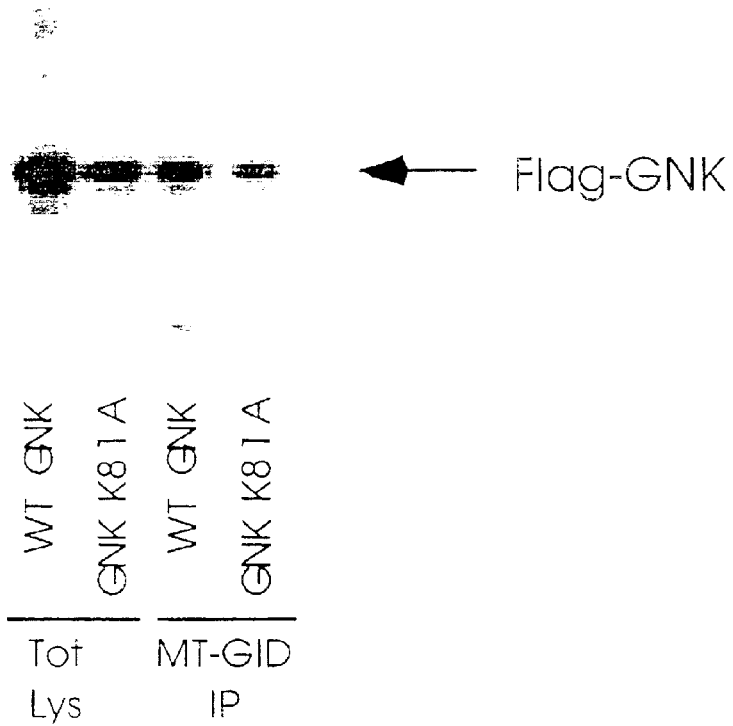
FIG. 3 is a Western Blot showing that GID can associate with GNK. A Myc-epitope tagged GID expression construct (MT-GID) was co-expressed in 293E cells with Flag-tagged wild-type (WT GNK) or a catalytically inactive mutant (GNK K81A) in the presence of sGNK. MT-GID was immunoprecipitated with anti-Myc. GNK was detected with an anti-Flag monoclonal antibody. The left two lanes indicate the expression of transfected GNK in cell lysates. The right two lanes indicate the presence of GNK in the MT-GID immunoprecipitates.
Figure 4:
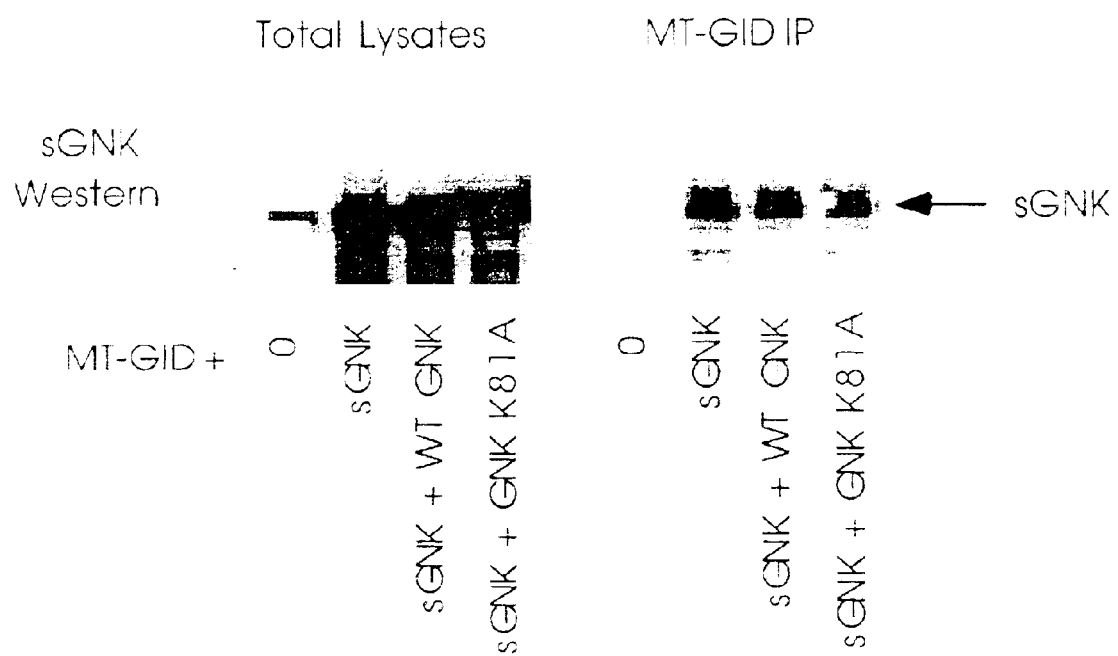
FIG. 4 is a Western Blot showing that GID can associate with sGNK. A Myc-epitope tagged GID expression construct (MT-GID) was generated and co-expressed in 293E cells as described for FIG. 3, with HA-tagged sGNK in the absence or presence of Flag-tagged wild-type (WT GNK) or a catalytically inactive mutant (GNK K81A). MT-GID was immunoprecipitated with anti-Myc. Immunoprecipitated GID was analyzed using an anti-sGNK polyclonal antibody. The left blot indicates the expression of endogenous and overexpressed sGNK in cell lysates. The right blot indicates the presence of sGNK in the MT-GID immunoprecipitates.
Figure 5:
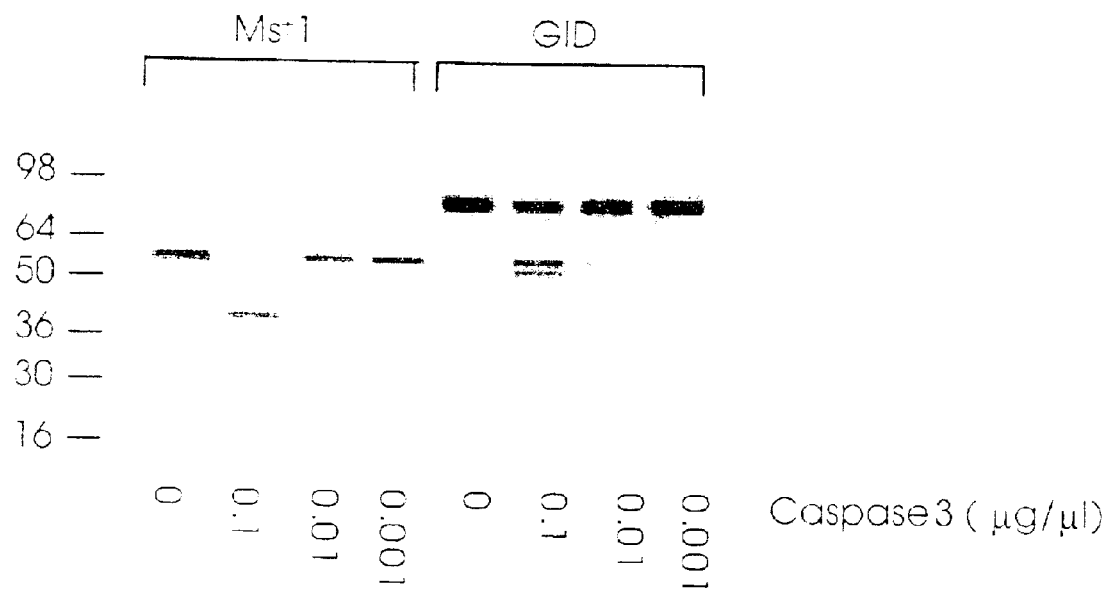
FIG. 5 shows the results of an in vitro caspase-3 assay. GID and Mst1 were translated in vitro using a coupled transcription and translation system (Promega). Mst1 was used as a positive control. As indicated, various amounts of recombinant caspase-3 (Pharmingen) was incubated with 1.5 µl of $^{35}$S-labeled in vitro translated Mst1, or GID as described in the Example below. Reactions were stopped by the addition of Laemmli sample buffer and subjected to SDS-PAGE prior to drying and autoradiography.

To determine if GID can associate with GNK, a Myc-epitope tagged GID expression construct (MT-GID) was co-expressed in 293E cells with Flag-tagged wild-type (WT GNK) or a catalytically inactive mutant (GNK K81A) in the presence of sGNK. Immunoprecipitated GID was analyzed by Western blotting for the presence of associated GNK using an anti-Flag monoclonal antibody (FIG. 3). The left two lanes indicate the expression of transfected GNK in the cell lysates. The right two lanes indicate the presence of GNK in the MT-GID immunoprecipitates. This result demonstrates that both wild-type or catalytically inactive GNK are capable of binding GID in cells.

293 Ebna cells were cultured in Dulbecco's modified Eagle medium supplemented with 10% fetal bovine serum and antibiotics. Three μg of each plasmid DNA was transfected into a 10 cm dish and cells were harvested two days after transfection. For immunoprecipitations, cells were washed once with cold PBS and lysed on ice in a buffer containing 50 mM Hepes, pH 7.4, 5 mM MnCl2, 10 mM MgCl2, 5 mM EGTA, 2 mM EDTA, 100 mM NaCl, 5 mM KCl, 1% Nonidet P-40, 30 μg/ml Rnase A, 1 mM PMSF, 1 μg/ml leupeptin, 0.1% aprotinin, 1 μg/ml heparin, 100 mM NaF, 20 mM β-glycerophosphate, 1 mM DTT and 0.1 mM Na3VO4. MT-GID was immunoprecipitated for 90 minutes at 4° C. with anti-Myc (9E10). Immune complexes were recovered using Protein A Sepharose beads coated with goat anti-mouse IgG. Complexes were washed three times in lysis buffer and once with wash buffer containing 20 mM Tris-HCl, pH 7.5, 25 mM β-glycerophosphate, 2 mM EGTA, 2 mM DTT and 1 mM Na3VO4 and then mixed with Laemmli sample buffer. Expression of polypeptides associated with MT-GID was determined by SDS-PAGE and Western blot analysis with the indicated antibodies.

GID can Associate with sGNK in 293 Cells in the Presence or Absence of GNK

To determine if GID can associate with sGNK, a Myc-epitope tagged GID expression construct (MT-GID) was generated and co-expressed in 293E cells with HA-tagged sGNK in the absence or presence of Flag-tagged wild-type (WT GNK) or a catalytically inactive mutant (GNK K81A). Immunoprecipitated GID was analyzed by Western blotting for the presence of associated sGNK using an anti-sGNK polyclonal antibody. The left blot indicates the expression of endogenous and overexpressed sGNK in the cell lysates. The right blot indicates the presence of sGNK in the MT-GID immunoprecipitates. The results demonstrate that sGNK is equally capable of binding GID in cells in the presence or absence of either wild-type or catalytically inactive GNK.

GID is Cleaved by Caspase-3 In Vitro: A Putative Consensus Sequence for Caspase-3 Cleavage was Identified in the GID Amino Acid Sequence Cleavage of the sequence DNVD (SEQ ID NO:27), located at position 581–584, would result in two fragments of approximately 60 kDa and 30 kDa. To determine if this was a bonafide caspase-3 cleavage site, an in vitro caspase-3 assay was performed. Cleavage of GID at the predicted sequence would remove the C-terminal coiled-coil domain from GID and separate it from the putative decarboxylase domain.

For the assay, GID and Mst1 were translated in vitro using a coupled transcription and translation system (Promega). Mst1 is a known caspase-3 target and was used as a positive control [Graves et al., EMBO 17:2224–2234 (1998)]. Indicated amounts of recombinant caspase-3 (Pharmingen) were incubated with 1.5 μl of $^{35}$S-labeled in vitro translated Mst1 or GID in 50 mM NaCl, 40 mM β-glycerophosphate, 10 mM Hepes, pH 7.4, 5 mM EGTA, 2 mM MgCl2 and 10 mM DTT in 10 μl for 1 hour at 37° C. Reactions were stopped by the addition of Laemmli sample buffer and subjected to SDS-PAGE prior to drying and autoradiography.

Increasing amounts of caspase-3 incubated with GID resulted in greater amounts of a cleavage product of approximately 58 kDa, which was not observed in the presence of incubation with buffer alone. This indicates that caspase-3 specifically cleaves GID in vitro, and the sizes of the resulting cleavage products are consistent with the cleavage site being at position 581–584 in GID.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are incorporated by reference in their entireties.

What is claimed is:

1. An isolated polypeptide comprising an amino acid sequence that is at least 95% identical to the contiguous amino acid residues 216 through 395 of SEQ ID NO: 2, said polypeptide having a decarboxylase activity.

2. An isolated polypeptide comprising an amino acid sequence of SEQ ID NO; 2, or a polypeptide fragment thereof, said polypeptide or polypeptide fragment having a decarboxylase activity.

3. An isolated polypeptide having a decarboxylase activity, wherein said polypeptide is encoded by a nucleic acid selected from the group consisting of:
   (a) a nucleic acid comprising nucleotides 646 through 1185 of SEQ ID NO: 1;
   (b) a nucleic acid, wherein the $T_m$ of a hybrid between said nucleic acid and that of a) is greater than 65° C.; and
   (c) a nucleic acid that, due to degeneracy of the genetic code, encodes a polypeptide encoded by (a) or (b).

4. The isolated polypeptide of claim 3 which is capable of binding to GNK and/or sGNK.

5. The isolated polypeptide of claim 3 which lacks a caspase-3 cleavage site.

6. The isolated polypeptide of claim 1, wherein said polypeptide is reactive to an antibody that binds specifically to an GID polypeptide comprising the amino acid sequence of SEQ ID NO: 2.

7. A fusion polypeptide comprising the polypeptide of claim 1, said fusion polypeptide having a decarboxylase activity.

8. A solid support comprising a polypeptide of claim 1 or a fragment thereof capable of binding GNK and/or sGNK.

9. A method of isolating GNK and/or sGNK from a sample that contains GNK or sGNK comprising:
   (a) passing the sample over the solid support of claim 8 under conditions in which GNK and/or sGNK bind to the solid support;
   (b) washing the solid support; and
   (c) eluting the GNK and/or sGNK, wherein said GNK and/or sGNK are isolated from the sample.

10. The method of claim 9 wherein the sample is a mammalian tissue sample.

11. A method of detecting caspase-3 activity in a sample comprising:
    (a) contacting the sample with the GID polypeptide of claim 2; and
    (b) detecting whether the GID polypeptide is cleaved; wherein the sample is determined to contain caspase-3 activity when the GID polypeptide is cleaved.

12. The method of claim 11 wherein the sample is a mammalian tissue sample.

13. The method of claim 11 wherein the cleavage of the GID polypeptide is detected using an antibody.

* * * * *